(12) United States Patent
Lu

(10) Patent No.: US 12,414,776 B2
(45) Date of Patent: Sep. 16, 2025

(54) CLIP DELIVERY DEVICE, AND RELEASING METHOD OF CLIP UNIT

(71) Applicant: OLYMPUS MEDICAL SYSTEMS CORP., Tokyo (JP)

(72) Inventor: Ranwen Lu, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 395 days.

(21) Appl. No.: 18/114,318

(22) Filed: Feb. 27, 2023

(65) Prior Publication Data

US 2023/0277190 A1 Sep. 7, 2023

Related U.S. Application Data

(60) Provisional application No. 63/315,433, filed on Mar. 1, 2022.

(51) Int. Cl.
*A61B 17/122* (2006.01)
*A61B 17/128* (2006.01)
*A61B 17/00* (2006.01)

(52) U.S. Cl.
CPC ........ *A61B 17/122* (2013.01); *A61B 17/1285* (2013.01); *A61B 2017/00296* (2013.01)

(58) Field of Classification Search
CPC .............. A61B 17/122; A61B 17/1285; A61B 17/1227; A61B 17/1222; A61B 2017/00296; A61B 2017/00292; A61B 2017/0034; A61B 2017/00477; A61B 2017/12004

See application file for complete search history.

(56) References Cited

U.S. PATENT DOCUMENTS 11,020,125 B2  6/2021  Randhawa et al.

FOREIGN PATENT DOCUMENTS

JP  2021-035501 A  3/2021

*Primary Examiner* — Ryan J. Severson
(74) *Attorney, Agent, or Firm* — Morgan, Lewis & Bockius LLP

(57) ABSTRACT

Clip delivery device has a sheath, a wire inserted into the sheath, and a clip detachably connected to the wire and having arms movable between an open position and a closed position. A tube is adjacent the sheath along a longitudinal axis and contains at least part of the clip and has a convex portion on an inner surface. A connector provided in the sheath has a hook detachably connected with the convex portion. The hook is movable between a first position, in which the hook engages the convex portion and is at a first radial distance from a central axis of the sheath, and a second position, in which the hook is disengaged from the convex portion and is at a second radial distance from the central axis of the sheath, where the first radial distance is greater than the second radial distance, by moving the wire.

20 Claims, 17 Drawing Sheets

CLIP DELIVERY DEVICE, AND RELEASING METHOD OF CLIP UNIT

CROSS-REFERENCE TO RELATED APPLICATIONS

The present disclosure claims priority on U.S. Provisional Application No. 63/315,433, filed Mar. 1, 2022. The disclosure of the prior applications is hereby incorporated by reference herein in its entirety.

TECHNICAL FIELD

The present disclosure relates to a clip delivery device, and a method of releasing a clip unit.

BACKGROUND

In an endoscopic treatment, a clip unit capable of ligating the dissection portion or the like after the treatment to realize the hemostasis or the like is used. The clip unit includes a clip configured to clamp the dissection portion or the like and a pressing tube configured to accommodate the clip and lock the clip in a closed state. The clip unit is introduced to the treatment portion by an applicator that is insertable into a channel of the endoscope.

The clip system disclosed in Japanese Unexamined Patent Application, First Publication No. 2021/035501 includes a clip assembly and an applicator having a mechanism into which the clip assembly is loadable and from which the clip assembly is detachable. The clip system is configured to be capable of reloading (reloadable) a new clip assembly to the applicator after indwelling the clip assembly in the living body.

SUMMARY

A clip delivery device comprises a sheath, a wire inserted into the sheath and a clip detachably connected to the wire and including a plurality of arms. The plurality of arms is movable between an open position and a closed position. The clip delivery device further comprises a tube containing at least part of the clip and having a convex portion on an inner surface of the tube and a connector provided in the sheath and having a hook. The hook detachably connected with the convex portion of the tube. The tube is adjacent the sheath along a longitudinal axis. The hook is movable between a first position and a second position. In the first position, the hook engages the convex portion of the tube and is located at a first radial distance from a central axis of the sheath. In the second position, the hook is disengaged from the convex portion of the tube and is located at a second radial distance from the central axis of the sheath. The first radial distance is greater than the second radial distance. When the wire is moved proximal to the sheath, the hook is moved from the first position to the second position.

A clip delivery device comprises a sheath, a wire inserted into the sheath and a clip detachably connected to the wire and including a plurality of arms. The plurality of arms is movable between an open position and a closed position. The clip delivery device further comprises a tube containing at least part of the clip and having a convex portion on an inner surface of the tube and a connector provided in the sheath and having a distal-end portion and a deformation portion. The distal-end portion is detachably connected to the convex portion on an inner surface of the tube. The deformation portion is elastically deformable. When the wire is moved proximal to the sheath, the deformation portion is elastically deformed to decrease a diameter of the distal-end portion of the connector.

DETAILED DESCRIPTION

First Embodiment

A clip delivery device 300 according to a first embodiment of the present disclosure will be described with reference from FIG. 1 to FIG. 13.

[Clip Delivery Device 300]

The clip delivery device (clip system, clip device) 300 includes a clip introduction device (applicator) 200 and a clip unit 1. The clip unit 1 is loaded into the clip introduction device 200.

[Clip Introduction Device 200]

Figure 1:
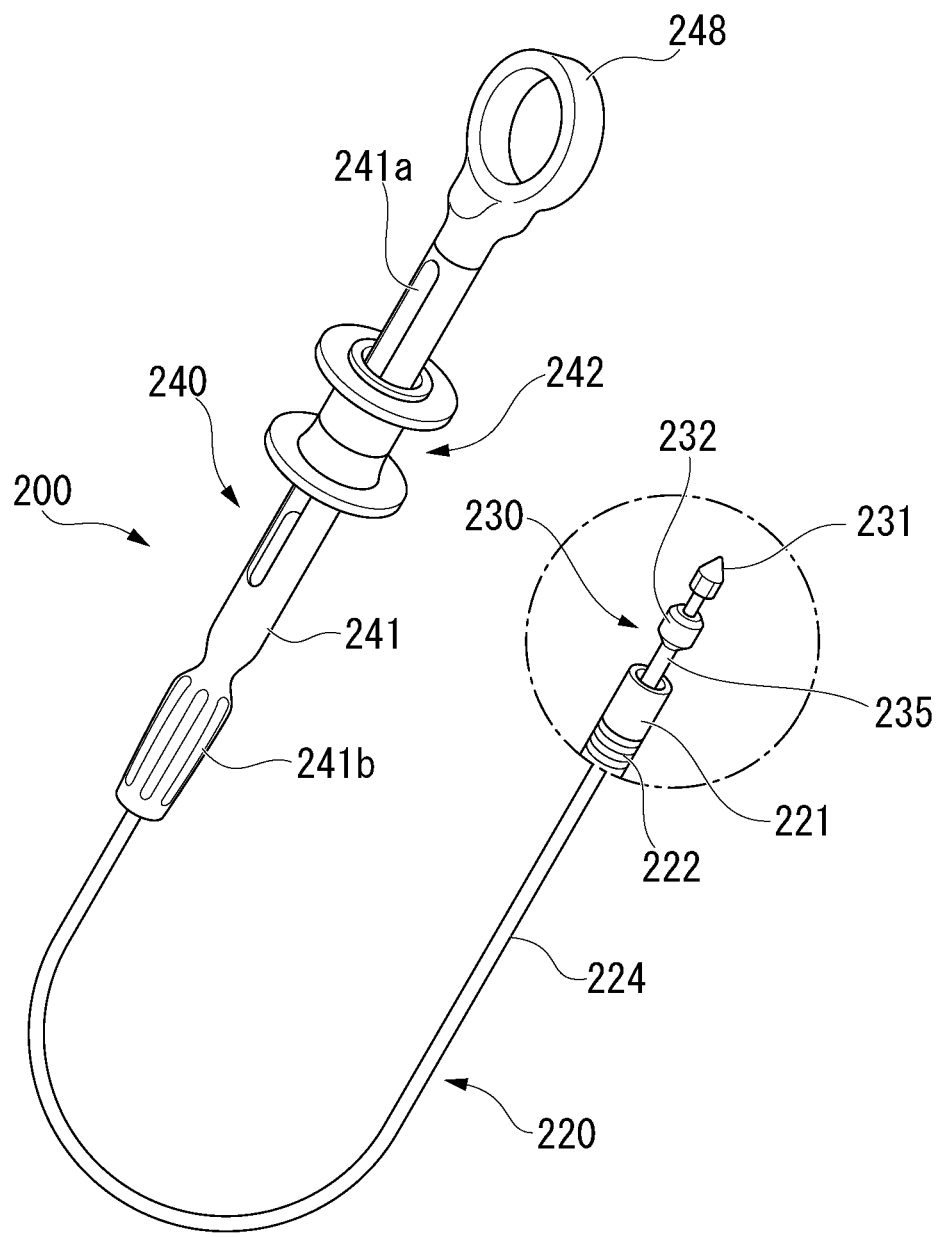
FIG. 1 is a view showing a clip introduction device of a clip delivery device according to a first embodiment.

FIG. 1 is a view showing the clip introduction device 200.

The clip introduction device (applicator) 200 includes a sheath 220, an operation wire 230, an operation portion 240, and a connection member (connector) 250.

In the following description, the clip unit 1 side in the longitudinal direction A of the clip delivery device 300 is referred to as a tip-end side (distal-end side) A1 of the clip delivery device 300, and the operation portion 240 side of the clip introduction device 200 is referred to as a base-end side (proximal-end side) A2 of the clip delivery device 300.

The clip introduction device 200 is, for example, inserted through the treatment device insertion channel of the endoscope to be used in combination with the endoscope. Accordingly, the sheath 220 is formed to be enough longer than the length of the treatment device insertion channel of the endoscope. The sheath 220 has the flexibility and is configured to bend following the bending of the insertion portion of the endoscope.

The sheath 220 includes a distal-end tube portion 221, a distal-end coil 222, and a hand-side coil 224, and the entire of the sheath 220 is formed in an elongated tubular shape. The distal-end coil 222 is disposed at the distal-end portion side of the sheath 220. The distal-end tube portion 221 is disposed in the distal-end portion of the distal-end coil 222.

As shown in FIG. 1, the operation wire (power transmission member) 230 includes an arrowhead hook (connection portion) connected to the clip unit 1, an enlarged-diameter portion 232, and a wire 235 to operate the arrowhead hook 231.

The arrowhead hook 231 is provided at the distal end of the operation wire (power transmission member) 230, and formed in the approximately conical shape. The arrowhead hook 231 is formed of metal material such as the stainless steel or the like, for example.

The enlarged-diameter portion 232 is provided at the proximal-end side A2 of the arrowhead hook 231. An outer diameter of the enlarged-diameter portion 232 is larger than an outer diameter of the wire 235. The enlarged-diameter portion 232 is formed of metal material such as the stainless steel or the like, for example.

The wire 235 is inserted to be freely advanceable and retractable with respect to the sheath 220. The distal-end portion of the wire 235 is fixed to the proximal end of the enlarged-diameter portion 232 by welding or the like, for example.

As shown in FIG. 1, the operation portion 240 includes an operation portion main body 241, a slider 242, and a thumb ring 248. The operation portion main body 241 is injection-molded, for example, from a resin material. The operation portion main body 241 includes a slit portion 241a, and a rotation grip 241b at the distal-end side. The slit portion 241a supports the slider 242 to be advanceable and retractable.

The slider 242 is attached to the operation portion main body 241 to be advanceable and retractable in the longitudinal direction, and to which the proximal end of the wire 235 is attached. By the slider 242 advancing and retracting along the operation portion main body 241, the wire 235 advances and retracts with respect to the sheath 220 and the arrowhead hook 231 advances and retracts.

The thumb ring 248 is attached to the proximal end of the operation portion main body 241 to be rotatable around the longitudinal direction of the operation portion main body 241.

[Connection Member 250]

Figure 2:
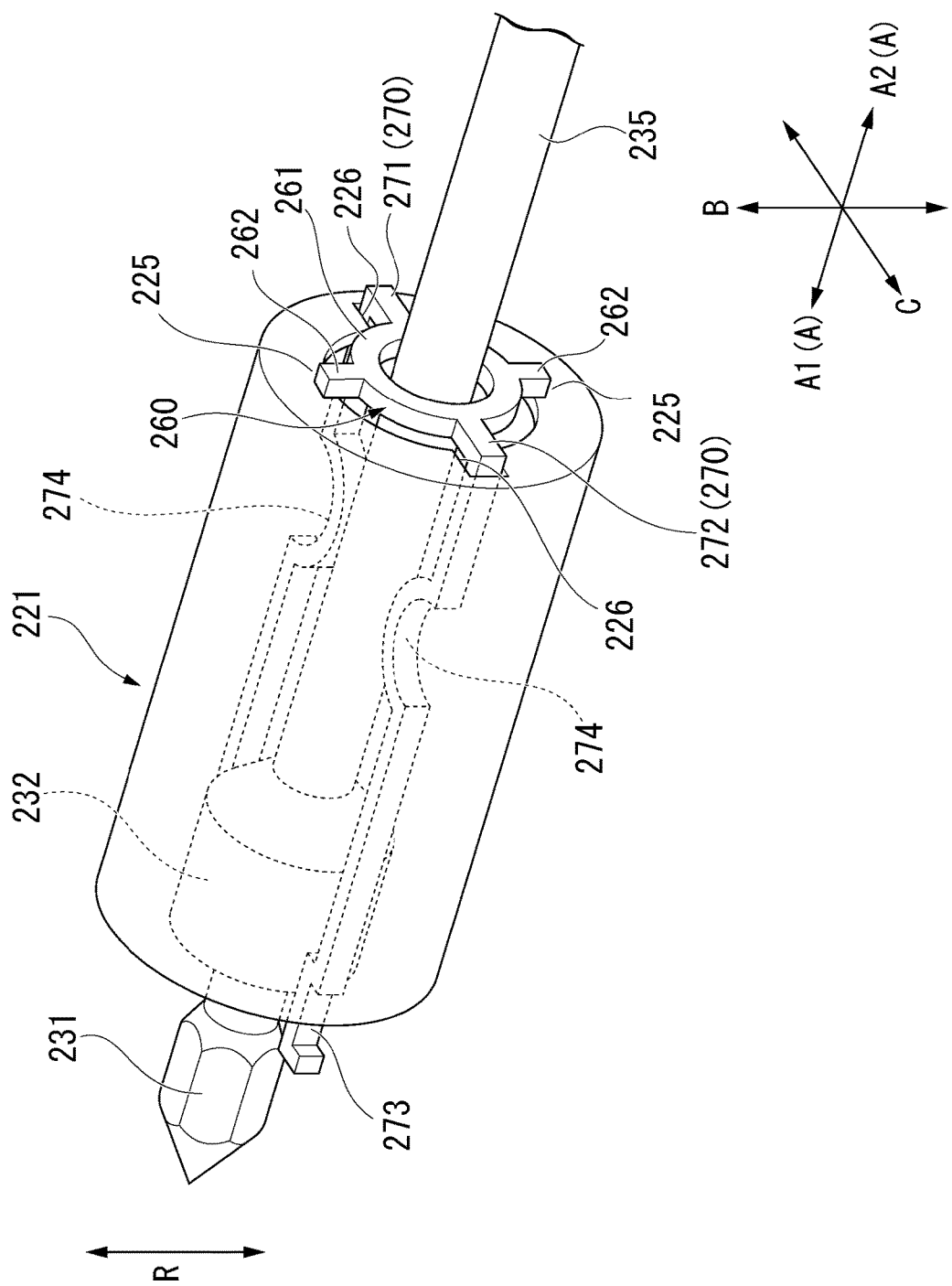
FIG. 2 is a perspective view showing a distal-end tube portion and a connection member of the clip introduction device.

FIG. 2 is a perspective view showing the distal-end tube portion 221 and the connection member 250.

The connection member 250 is a member for detachably connecting the clip unit 1 and the clip introduction device 200, and the connection member 250 is provided in the internal space of the distal-end tube portion 221.

Figure 3:
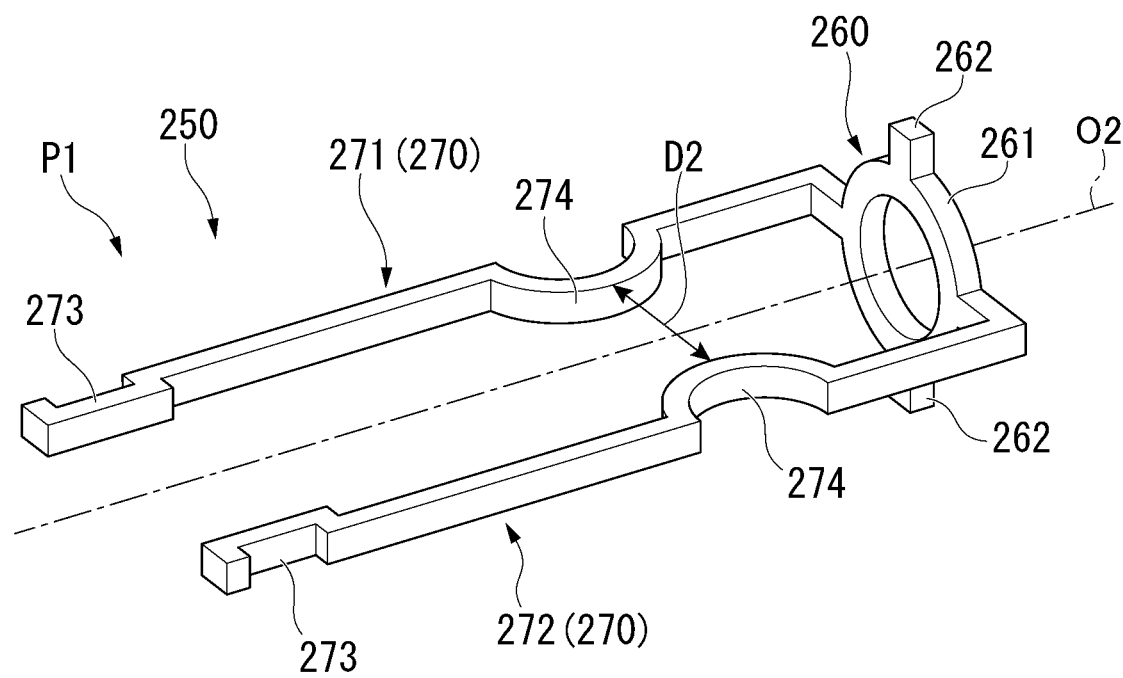
FIG. 3 is a perspective view showing the connection member.
Figure 3:
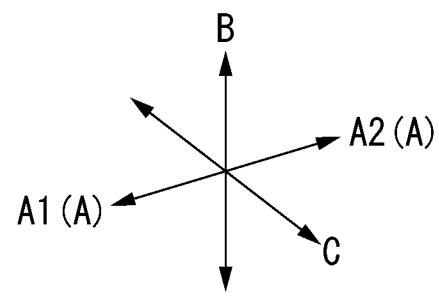

FIG. 3 is a perspective view showing the connection member 250.

The connection member 250 includes a support portion (support base) 260 and a connection arm 270. In the present embodiment, the connection arm 270 includes a first connection arm 271 and a second connection arm 272. The connection arm 270 may include three or more connection arms.

The support portion 260 is a member that is supported by the distal-end tube portion 221. The support portion 260 includes an annular portion 261 and an engagement convex portion 262.

As shown in FIG. 2, the annular portion 261 is formed in an annular shape such that the wire 235 can pass through the internal space thereof. The outer diameter D1 of the enlarged-diameter portion 232 is larger than an inner diameter of the annular portion 261, and it is impossible for the enlarged-diameter portion 232 to pass through the internal space of the annular portion 261.

The engagement convex portion 262 is a convex portion protruding outwardly in the radial direction R from the annular portion 261. The engagement convex portion 262 is provided at both sides in the up-down direction B orthogonal to the longitudinal direction A.

The distal-end tube portion 221 has a proximal-end opening portion 225 at the proximal-end side A2. The proximal-end opening portion 225, for example, is a convex portion protruding toward the inside in the radial direction R from the inner circumferential surface of the distal-end tube portion 221. The proximal-end opening portion 225 as the example shown in FIG. 2 is formed across the whole circumference in the inner circumferential surface of the distal-end tube portion 221. The engagement convex portion 262 is engaged with the proximal-end opening portion 252 from the proximal-end side A2 so as to be impossible to move to the distal-end side A1 beyond the proximal-end opening portion 225.

The proximal-end portion of the connection arm 270 (first connection arm 271 and second connection arm 272) is attached to the support portion 260. More specifically, the proximal-end portion of the connection arm 270 is attached to the support portion 260 at both sides in the radial direction R. The connection arm 270 extends toward the distal-end side A1 from the support portion 260 passing through a slit 226 formed in the proximal-end opening portion 225.

The connection arm 270 is arranged at both sides in the left-right direction C orthogonal to the longitudinal direction A and the up-down direction B. The first connection arm 271 and the second connection arm 272 are formed in a shape symmetrical with respect to the central axis O2 in the longitudinal direction A of the connection member 250.

The connection arm (first connection arm 271 and second connection arm 272) includes a hooking portion (hook) 273 and a deformation portion 274.

The hooking portion (hook) 273 is a hook whose outside in the radial direction is formed in a concave portion, and is provided at the distal end of the connection arm 270. As shown in FIG. 2, the hooking portion 273 protrudes in the distal-end side A1 from the distal-end tube portion 221. The hooking portion 273 is engageable with the decreased-diameter portion 33 of the pressing tube 3 described below.

The deformation portion 274 is an intermediate portion of the connection arm 270, and is a portion bent in a C shape toward the inside in the radial direction R. The deformation portion 274 may be a portion bent in a semicircular or semioval toward the inside in the radial direction R. A distance D2 between the deformation portions 274 arranged at two sides to sandwich the central axis O2 is smaller than the outer diameter D1 of the enlarged-diameter portion 232 of the operation wire 230 (see FIG. 6).

The connection arm 270 (first connection arm 271 and second connection arm 272) is configured such that at least the deformation portion 274 has the elasticity and is movable at least in the left-right direction C. In the present embodiment, in the state without receiving any external force, the connection arm 270 is arranged at a position (hereinafter referred to as an initial position) where the first connection arm 271 and the second connection arm 272 are substantially parallel to each other.

[Clip Unit 1]

Figure 4:
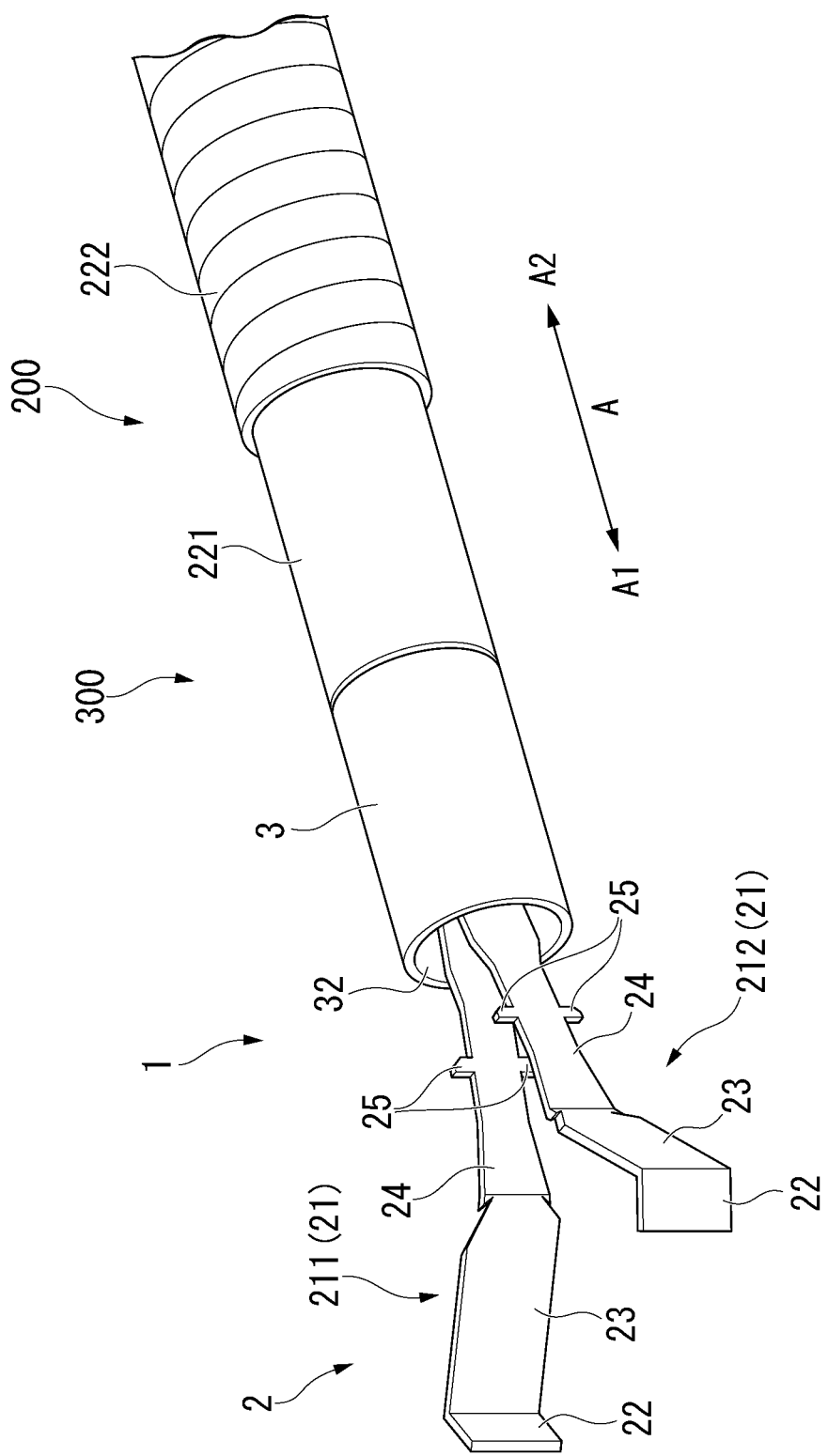
FIG. 4 is a perspective view showing a clip unit that is loaded in the clip introduction device.
Figure 5:
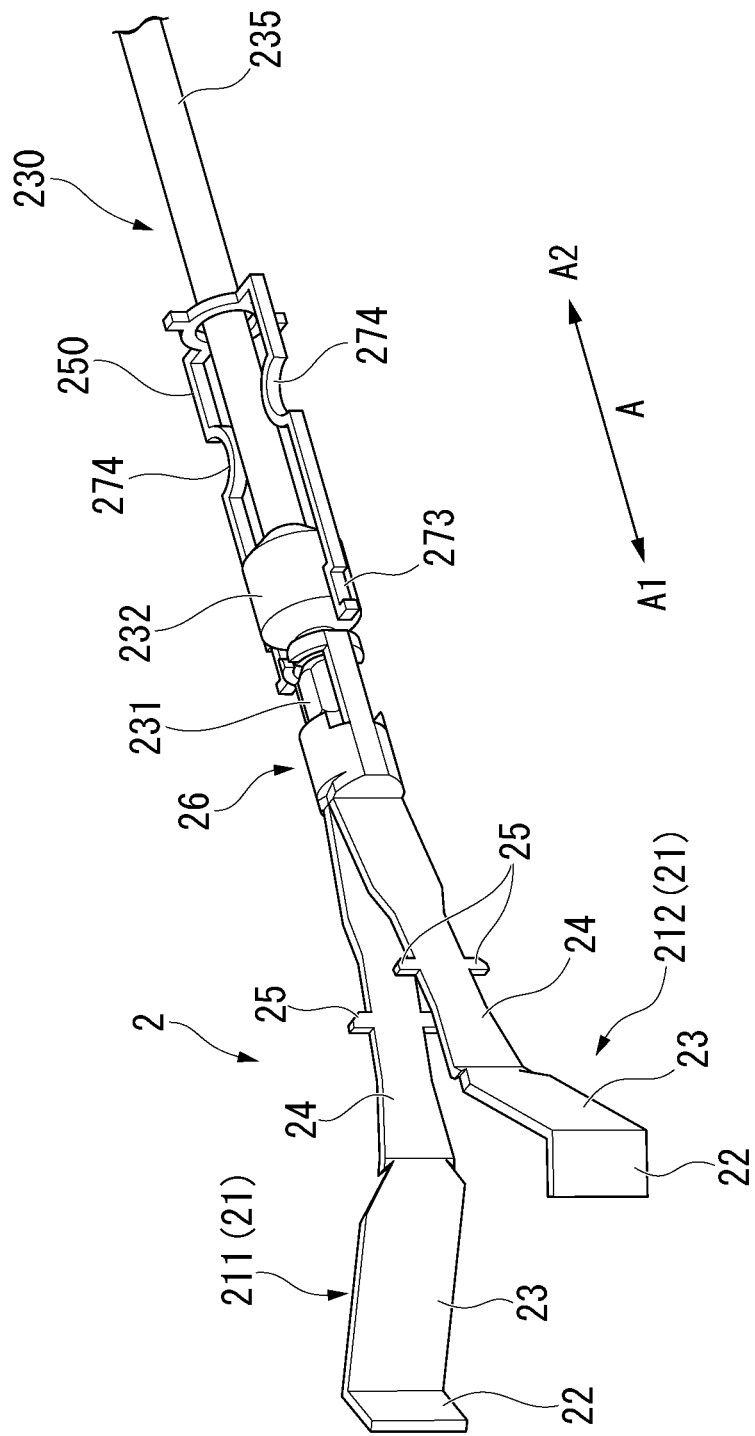
FIG. 5 is a perspective view showing a clip that is connected with an operation wire of the clip introduction device.
Figure 6:
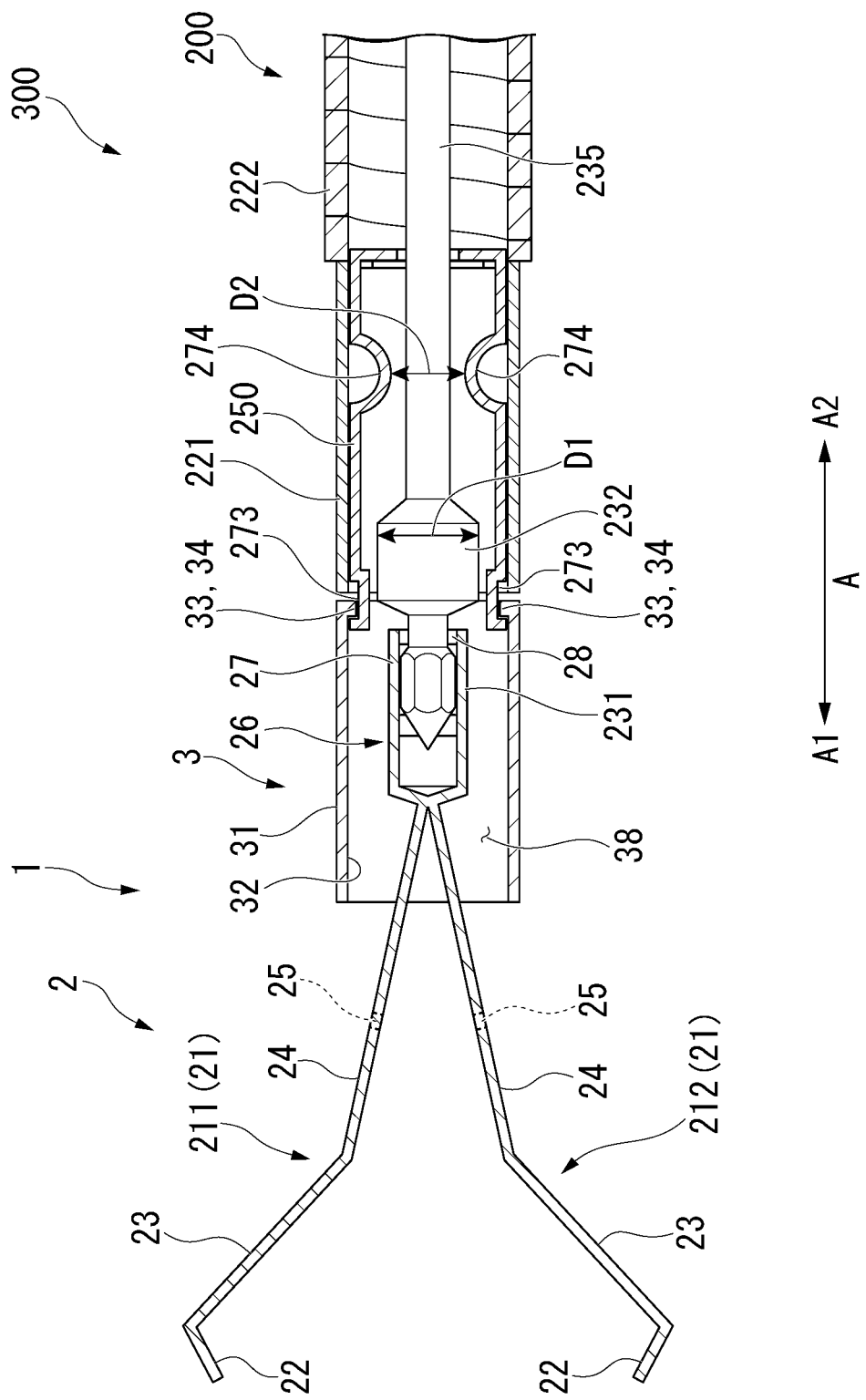
FIG. 6 is a cross-sectional view showing the clip unit that is loaded in the clip introduction device.

FIG. 4 is a perspective view showing the clip unit 1 that is loaded in the clip introduction device 200. FIG. 5 is a perspective view showing the clip 2 connected to the operation wire 230. FIG. 6 is a cross-sectional view showing the clip unit 1 that is loaded in the clip introduction device 200. The clip unit 1 includes the clip 2 and the pressing tube 3. The proximal-end side A2 of the clip 2 is inserted into the internal space 38 of the pressing tube 3.

Figure 7:
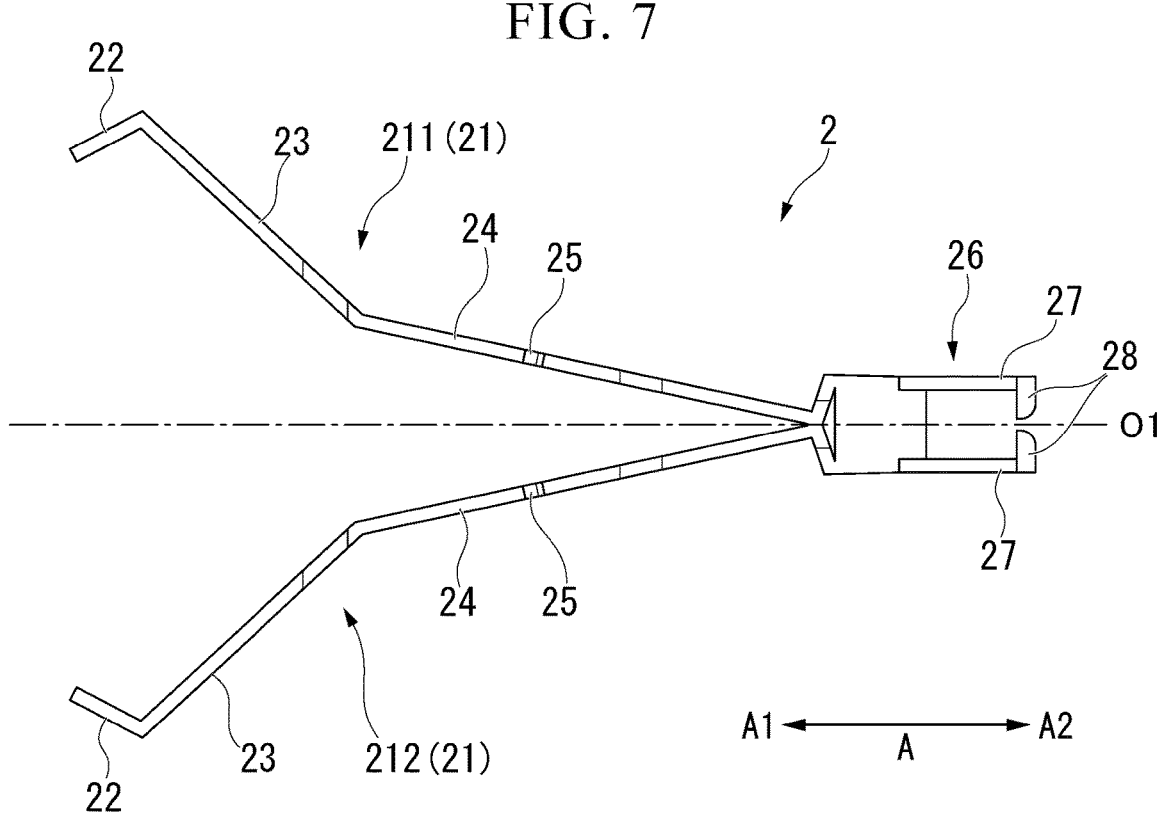
FIG. 7 is a planar view showing the clip of the clip unit.

FIG. 7 is a planar view showing the clip 2.

The clip 2 includes a pair of arms 21 that can be opened and closed toward the distal-end side A1, and a proximal-end portion 26 provided on the proximal-end side A2 of the pair of arms 21. As shown in FIG. 5 and FIG. 6, the clip 2 is detachably connected to an arrowhead hook 231 of the operation wire 230 being inserted through the sheath 220.

The pair of arms 21 has a first arm 211 and a second arm 212. The first arm 211 and the second arm 212 are arranged symmetrically with respect to a central axis O1 in the longitudinal direction A of the clip unit 1. It is noted that the clip 2 may have three or more arms.

The first arm 211 and the second arm 212 have a claw 22, a grasping portion 23, a sliding portion 24, and an engaging portion 25 arranged from the distal-end side A1 toward the proximal-end side A2.

The claw 22 is formed by bending the distal ends of the first arm 211 and the second arm 212 inwardly. The grasping portion 23 is formed in a substantially flat plate shape and is a portion that grasps the tissue. The sliding portion 24 is a portion that is elastically deformed when the pair of arms 21 is retracted into the pressing tube 3.

The engaging portion 25 is a portion that is engageable with the inner circumferential surface 32 of the pressing tube 3. The engaging portion 25 is a convex portion that protrudes from the sliding portion 24. Specifically, the engaging portion 25 protrudes to both sides in the up-down direction perpendicular to the longitudinal direction A and the open-close direction P of the pair of arms 21.

The proximal-end portion 26 is supported by the first arm 211 and the second arm 212. The first arm 211 and the second arm 212 supported by the proximal-end portion 26 is provided to be freely openable and closable toward the distal-end side A1. The proximal-end portion 26 is biased such that the pair of arms 21 are in the open state. Accordingly, the pair of arms 21 of the clip 2 have a self-expanding force in the open-close direction.

The proximal-end portion 26 is detachably connected with the arrowhead hook 231 inserting through the sheath 220. The proximal-end portion 26 includes a pair of connection arms 27 to be freely openable and closable with respect to the proximal-end side A2. The pair of connection arms 27 clamp the arrowhead hook 231. The pair of connection arms 27 include a pair of stoppers 28 protruding toward each other at the proximal end thereof.

The arrowhead hook 231 can pass through the gap between the pair of stoppers 28 by pressing the pair of stoppers 28 to expand in a direction separating from the central axis O1. The arrowhead hook 231 passes through the gap between the pair of stoppers 28 toward the distal-end side A1 so as to be connected with the connection arm 27. The arrowhead hook 231 passes through the gap between the pair of stoppers 28 toward the proximal-end side A1 so as to be separated from the connection arm 27.

The pressing tube (tubular member, tube) 3 is a circular tubular member capable of accommodating at least part of the clip 2. The pressing tube 3 has the internal space 38 where the clip 2 advances and retracts in the longitudinal direction A. The pressing tube 3 can fix the clip 2 in the closed state that is retracted into the internal space 38 thereof. The pressing tube 3 includes a pressing tube main body 31 formed in a cylindrical shape and a decreased-diameter portion 33.

The pressing tube main body 31 is formed by performing the injection molding using a material more flexible than that of the clip 2, for example, the thermoplastic resin such as PPA (polyphthalamide), PA (polyamide), PEEK (polyetheretherketone), LCP (liquid crystal polymer), and the like having appropriate elasticity. It is noted that the pressing tube main body 31 may be made of the metal instead of the thermoplastic resin.

The decreased-diameter portion (narrow portion, engaged portion) 33 is provided at the proximal-end side A1 of the pressing tube main body 31 to form a proximal-end opening 34. The inner diameter of the proximal-end opening 34 is smaller than the inner diameter of the pressing tube main body 31. The decreased-diameter portion 33, for example, is a convex portion protruding to the inside in the radial direction R and arranged along the circumferential direction in the inner circumferential surface 32. It is noted that the decreased-diameter portion 33 does not have to be formed across the whole circumference in the circumferential direction.

[Operations and Effect of Clip Delivery Device 300]

Next, the operations and effect of the clip delivery device 300 will be described by referring from FIG. 8 to FIG. 13.

Figure 8:
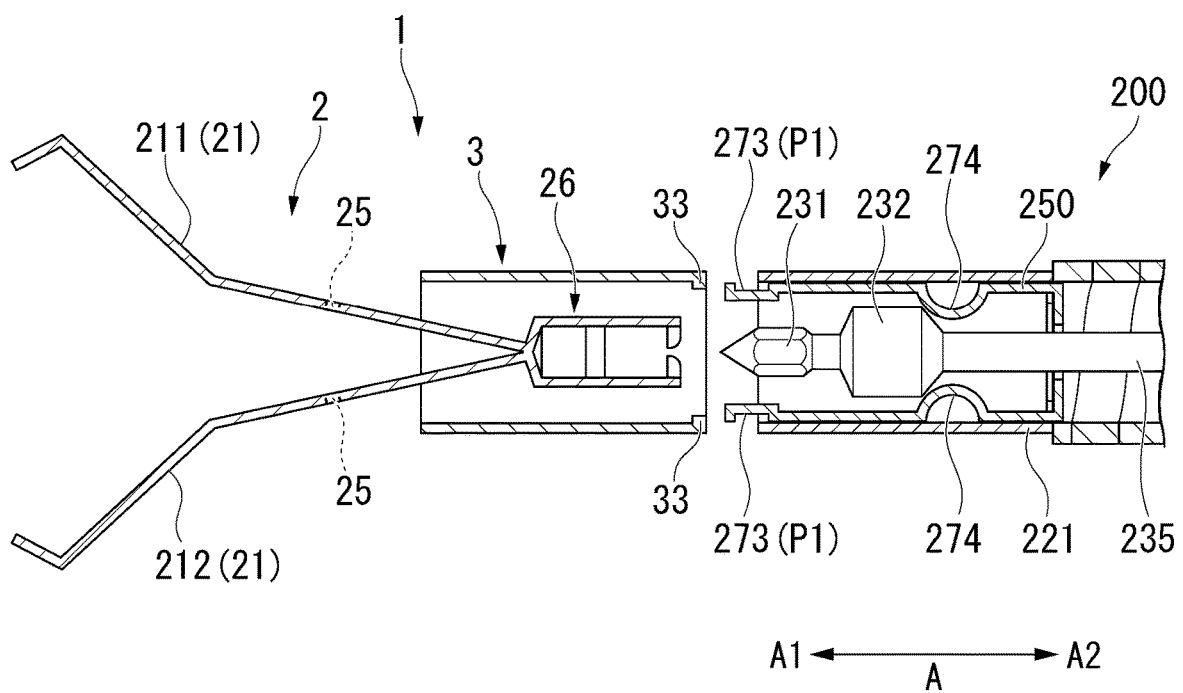
FIG. 8 is a cross-sectional view showing the clip introduction device before loading the clip unit.

FIG. 8 is a cross-sectional view showing the clip introduction device 200 before loading the clip unit 1. Before loading the clip unit 1, the connection arm 270 of the connection member 250 is disposed at the initial position. The enlarged-diameter portion 232 of the operation wire 230 is disposed at the distal-end side A1 with respect to the deformation portion 274 of the connection member 250.

Figure 9:
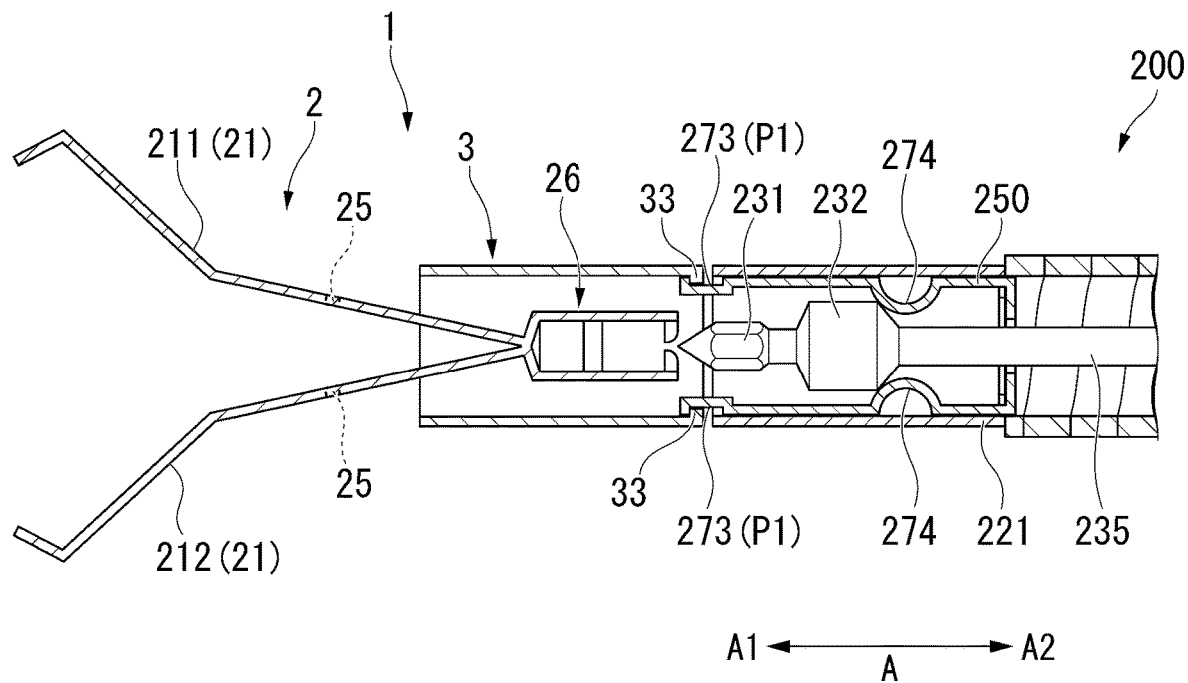
FIG. 9 is a cross-sectional view showing the clip introduction device that is connected with a pressing tube of the clip unit.

FIG. 9 is a cross-sectional view showing the clip introduction device 200 that is connected to the pressing tube 3. The user pushes the clip unit 1 toward the clip introduction device 200 from the distal-end side A1 so as to engage the hooking portion 273 protruding from the distal-end tube portion 221 toward the distal-end side A1 with the decreased-diameter portion 33 of the pressing tube 3. The connection member 250 has the elasticity so as to tend to return to the initial position. At this time, the hooking portion 273 moves outwardly in the radial direction to be disposed at a position (hereinafter referred to as a first position P1) where the hooking portion 273 engages with the decreased-diameter portion 33 from the inside of the radial direction. The decreased-diameter portion 33 is formed across the whole circumference in the inner circumferential surface 32 of the pressing tube main body 31. Accordingly, it is possible for the surgeon to make the hooking portion 273 and the decreased-diameter portion 33 to be definitely engaged with each other despite of the position of the hooking portion 273 in the circumferential direction C. The decreased-diameter portion 33 may be formed across at least a portion of the inner circumferential surface 32 of the pressing tube main body 31.

The user advances the operation wire 230 to connect the proximal-end portion 26 of the clip 2 and the arrowhead hook 231. As a result, the clip unit 1 is loaded inside the clip introduction device 200.

Figure 10:
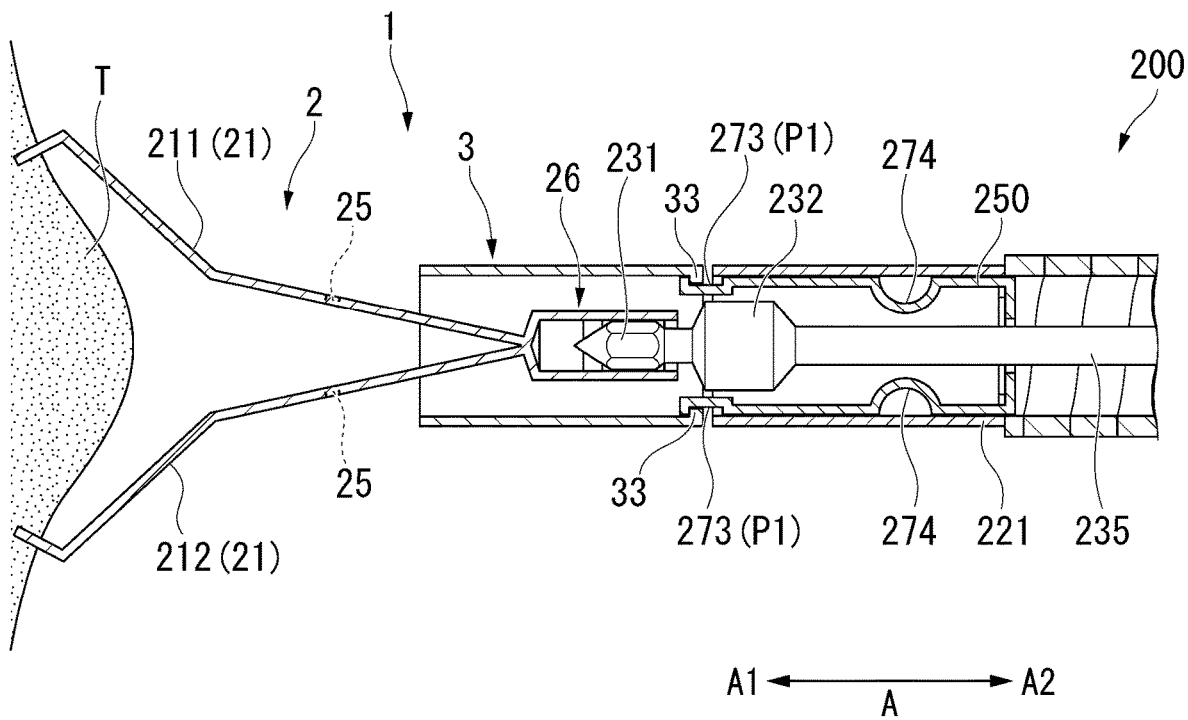
FIG. 10 is a cross-sectional view showing the clip introduction device into which the clip unit is loaded.

FIG. 10 is a cross-sectional view showing the clip introduction device 200 into which the clip unit 1 is loaded. The user introduces the clip unit 1 that is loaded in the clip introduction device 200 into the body through the channel of the endoscope. The user operates the operation portion 240 to grasp the tissue T by the clip 2.

The user retracts the slider 242 along the operation portion main body 241 to retract the clip 2 (traction step). By pulling the proximal-end portion 26 of the clip 2 to the proximal-end side A2, the pair of arms 21 are retracted into the pressing tube 3 and the pair of arms 21 are gradually closed. When the slider 242 is advanced along the operation portion main body 241 in this state, the arrowhead hook 231 is advanced. Since the proximal-end portion 26 of the clip 2 protrudes toward the distal-end side A1, the pair of arms 21 protrude from the pressing tube 3 and the pair of arms 21 gradually open. At this time, the decreased-diameter portion 33 of the pressing tube 3 is engaged with the hooking portion 273 such that the pressing tube 3 does not move toward the distal-end side A1. Accordingly, it is possible for the user to make the pair of arms 21 to return to the open state to re-grasp the tissue T (re-opening).

Figure 11:
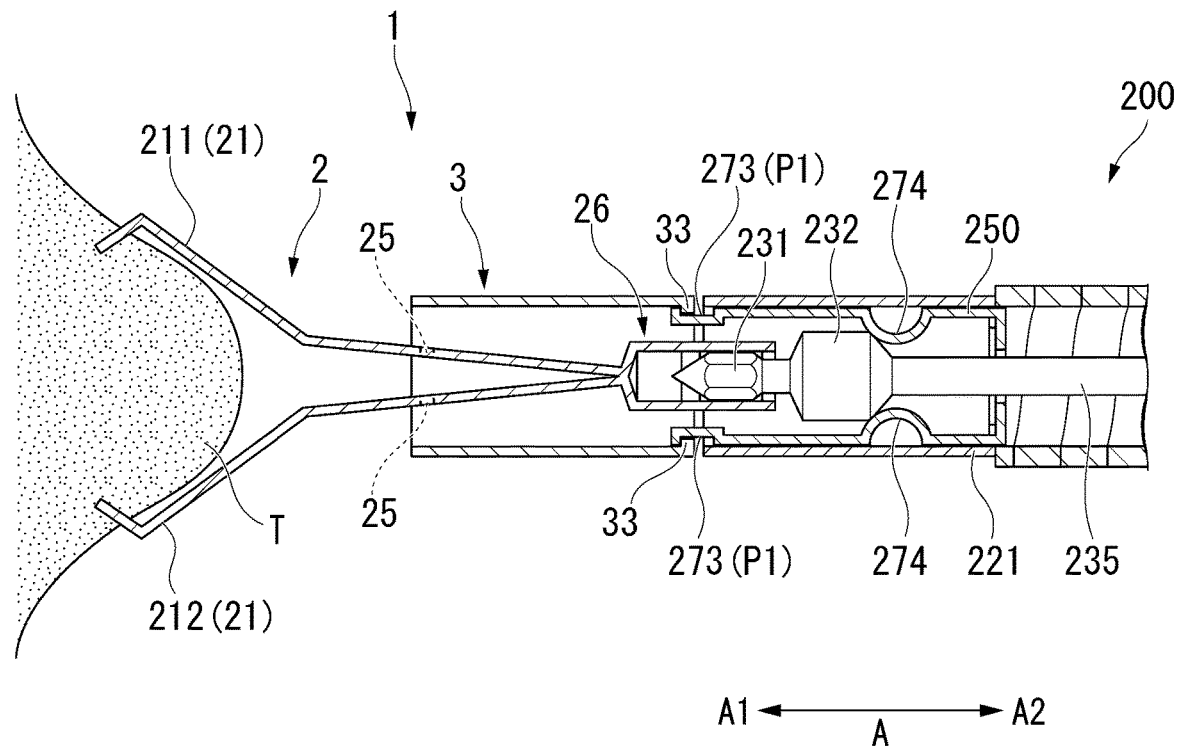
FIG. 11 is a cross-sectional view showing the clip unit where the clip is locked and the clip introduction device.

FIG. 11 is a cross-sectional view showing the clip unit 1 where the clip 2 is locked and the clip introduction device 200. By further pulling the proximal-end portion 26 toward the proximal-end side A2, the engaging portion 25 is retracted into the internal space 38 of the pressing tube 3. When the engaging portion 25 is retracted into the internal space 38 of the pressing tube 3, the engaging portion 25 and the inner circumferential surface 32 of the pressing tube 3 are engaged with each other. As a result, the movement of the clip 2 toward the distal-end side A1 with respect to the pressing tube 3 is restricted and the pair of arms 21 are locked in the closed state. When the pair of arms 21 are locked in the closed state, it is impossible for the pair of arms 21 to return to the open state.

Figure 12:
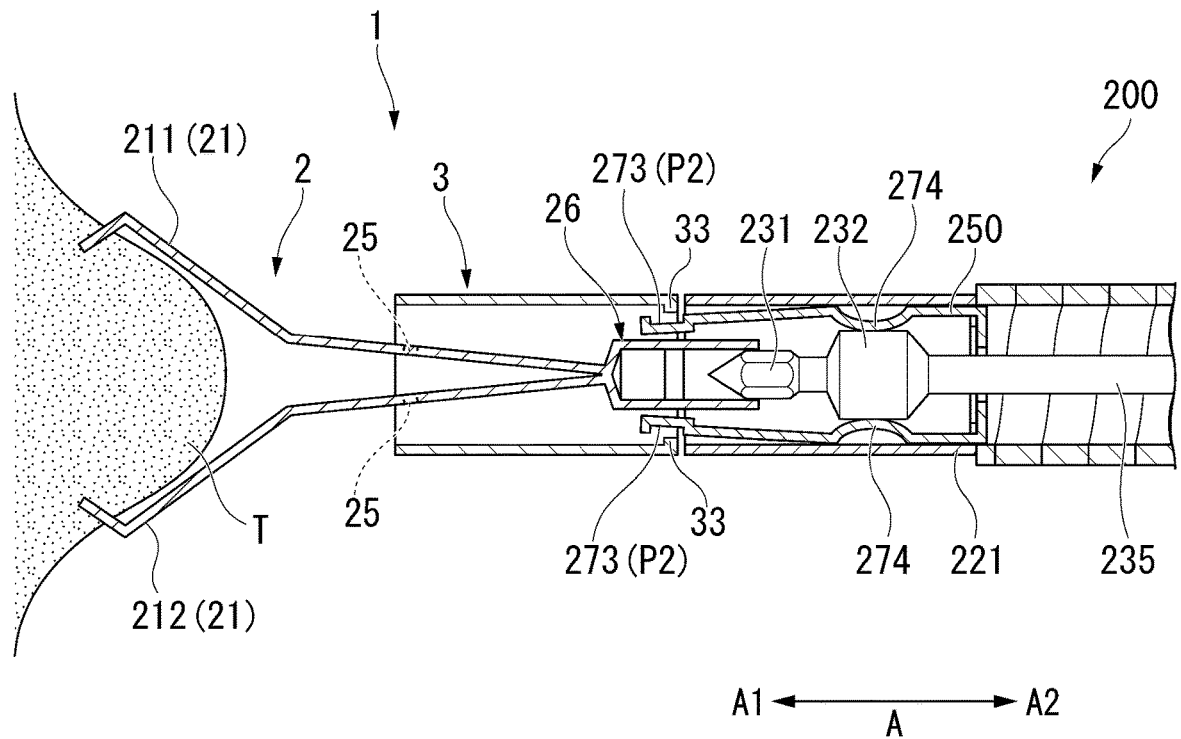
FIG. 12 is a cross-sectional view showing the clip introduction device where the arrowhead hook is further pulled.

FIG. 12 is a cross-sectional view showing the clip introduction device 200 where the arrowhead hook 231 is further pulled. The engaging portion 25 and the inner circumferential surface 32 of the pressing tube 3 are engaged with each other and the pair of arms 21 are locked in the closed state such that the clip 2 is not further pulled toward the proximal-end side A2. The arrowhead hook 231 of the pulled operation wire 230 is separated from the proximal-end portion 26 to be pulled toward the proximal-end side A2.

The enlarged-diameter portion 232 of the pulled operation wire 230 moves in the gap between the deformation portions 274 of the connection member 250 toward the proximal-end side A2. The distance D2 between the deformation portions 274 is smaller than the outer diameter D1 of the enlarged-diameter portion 232 of the operation wire 230 (D1>D2). Accordingly, the enlarged-diameter portion 232 comes into contact with the deformation portions 274 to make the deformation portions 274 to deform so as to extend along the longitudinal direction A. As a result, the hooking portion 273 at the distal-end side moves to a position (hereinafter referred to as a second position P2) at the inside in the radial direction with respect to the first position P1. In other words, the distal-end portion of the connection member 250 is decreased in the dimeter (diameter decreasing step). In other words, a first radial distance is greater than a second radial distance. The first radial distance is from hooking portion 273 to a central axis of the sheath 220 in the first position P1. The second radial distance is from hooking portion 273 to a central axis of the sheath 220 in the second position P2. The hooking portion 273 that is disposed at the second position P2 is in the state in which the hooking portion 273 is not engaged with the decreased-diameter portion 33, or the state in which the engagement with the decreased-diameter portion 33 is easy to be released.

Figure 13:
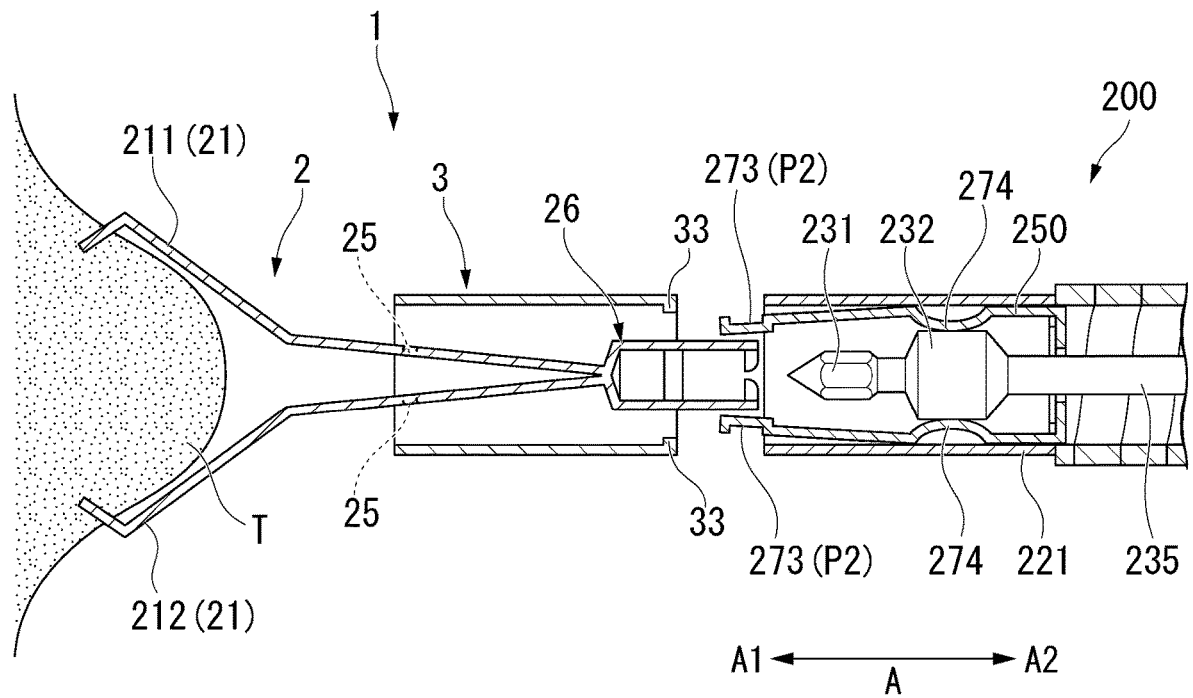
FIG. 13 is a cross-sectional view showing the clip introduction device from which the clip unit is separated.

FIG. 13 is a cross-sectional view showing the clip introduction device 200 from which the clip unit 1 is separated. The user further pulls the clip 2. The engagement between the decreased-diameter portion 33 and the hooking portion 273 is disengaged such that the clip unit 1 and the clip introduction device 200 are separated. The user retracts the sheath 220 to indwell the clip unit 1 in the state of ligating the tissue inside the body (indwelling step).

According to the clip delivery device 300 and the clip introduction device 200 according to the present embodiment, it is possible for the clip 2 of the clip unit 1 to re-grasp the tissue (re-opening) such that the loading and the separation of the clip unit 1 with respect to the clip introduction device 200 can be definitely performed.

As described above, the first embodiment of the present disclosure has been described in detail with reference to the drawings; however, the specific configuration is not limited to the present embodiment, and design changes and the like are included within the scope of the present disclosure. Also, the configurational elements shown in the present embodiment and the modification examples shown below can be combined as appropriate.

Second Embodiment

A second embodiment of the present disclosure will be described by referring from FIG. 14 to FIG. 20. In the following description, the described configurations and the common configurations will be designated with the same reference signs and the duplicate description will be omitted. The clip delivery device according to the second embodiment is different from the clip delivery device 300 according to the first embodiment in the connection member 250.

The clip delivery device according to the present embodiment includes a clip introduction device (applicator) 200B and the clip unit 1. The clip introduction device (applicator) 200B includes the sheath 220, an operation wire 230B, the operation portion 240, and a connection member 250B.

The operation wire (power transmission member) 230B includes the arrowhead hook 231, the enlarged-diameter portion 232, a second enlarged-diameter portion 233 provided at the proximal end with respect to the enlarged-diameter portion 232, and the wire 235. The outer diameter of the second enlarged-diameter portion 233 is larger than the inner diameter of the annular portion 261, and the second enlarged-diameter portion 233 is impossible to pass through the internal space of the annular portion 261.

Figure 14:
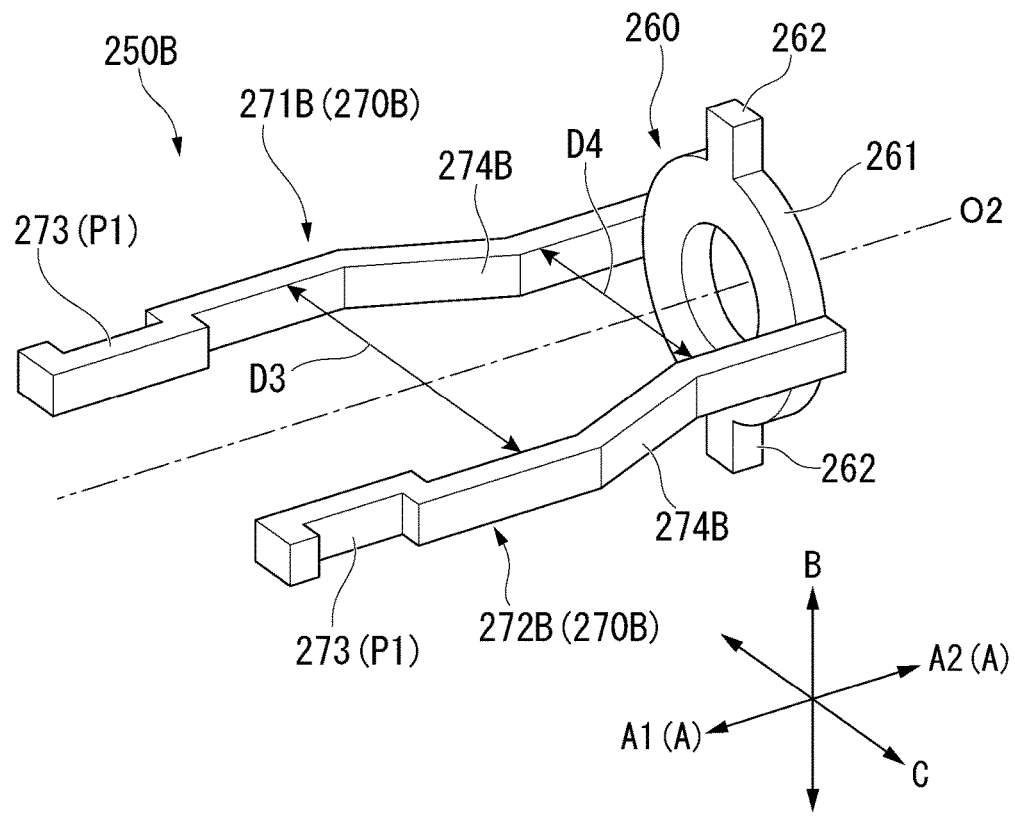
FIG. 14 is a perspective view showing a connection member in a clip introduction device of a clip delivery device according to a second embodiment.

FIG. 14 is a perspective view showing the connection portion 250B.

The connection portion 250B includes the support portion 260 and a connection arm 270B. The proximal end of the connection arm 270B (first connection arm 271B and second connection arm 272B) is attached to the support portion 260.

The connection arm 270B is arranged at both sides in the left-right direction C orthogonal to the longitudinal direction A and the up-down direction B. The first connection arm 271B and the second connection arm 272B are formed in a shape symmetrical with respect to the central axis O2 in the longitudinal direction A of the connection member 250B.

The connection arm 270B (first connection arm 271B and second connection arm 272B) includes the hooking portion 273 and a deformation portion 274B.

The deformation portion 274B is a tapered portion formed in an intermediate portion of the connection arm 270B. Specifically, the deformation portion 274B is formed in a tapered shape so as to approach the central axis O1 from the distal-end side A1 toward the proximal-end side A2. In other words, the distance D3 between the distal ends of the deformation portions 274B is larger than the distance D4 between the proximal ends of the deformation portions 274B (D3>D4).

The distance D3 between the distal ends of the deformation portions 274B is larger than the outer diameter D5 of the proximal-end opening portion 225 (D3>D5). In the present embodiment, the outer diameter D1 of the enlarged-diameter portion 232 of the operation wire 230B is smaller than the outer diameter D5 of the proximal-end opening portion 225 (D5>D1). Accordingly, the enlarged-diameter portion 232 can pass through the proximal-end opening portion 225.

The connection arm 270B (first connection arm 271B and second connection arm 272B) is configured such that at least the deformation portion 274B has the elasticity and is movable at least in the left-right direction C. In the present embodiment, in the state without receiving any external force, the connection arm 270B is arranged at a position (the initial position) where the first connection arm 271B and the second connection arm 272B are substantially parallel to each other.

Next, the operations and effect of the clip delivery device according to the present embodiment will be described by referring from FIG. 15 to FIG. 20.

Figure 15:
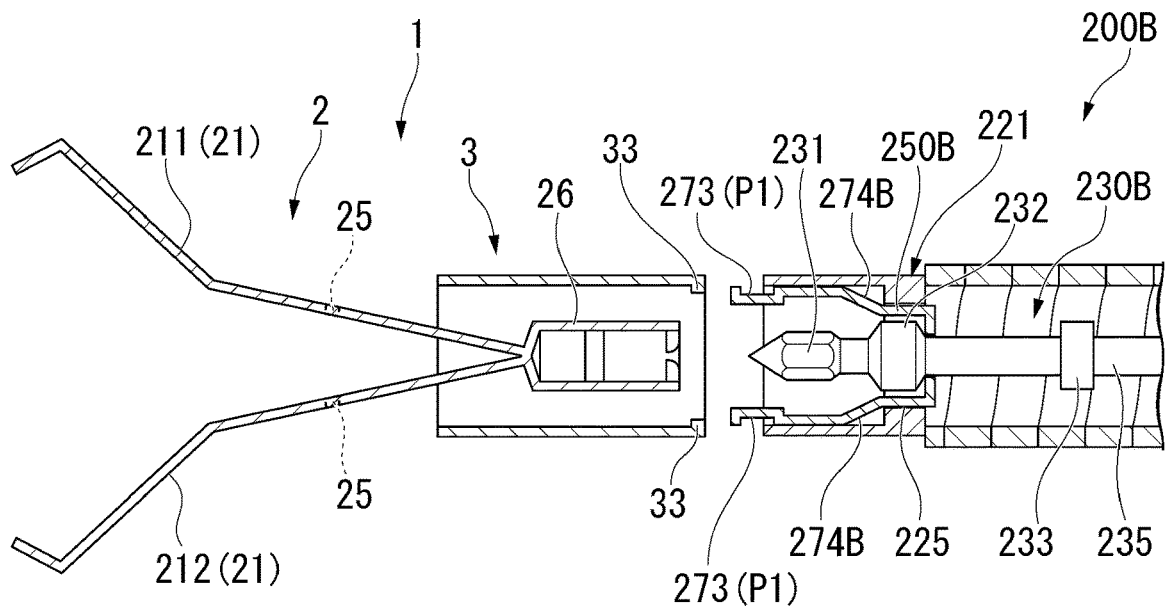
FIG. 15 is a cross-sectional view showing the clip introduction device before loading the clip unit.

FIG. 15 is a cross-sectional view showing the clip introduction device 200B before loading the clip unit 1. Before loading the clip unit 1, the connection arm 270B of the connection member 250B is disposed at the initial position.

Figure 16:
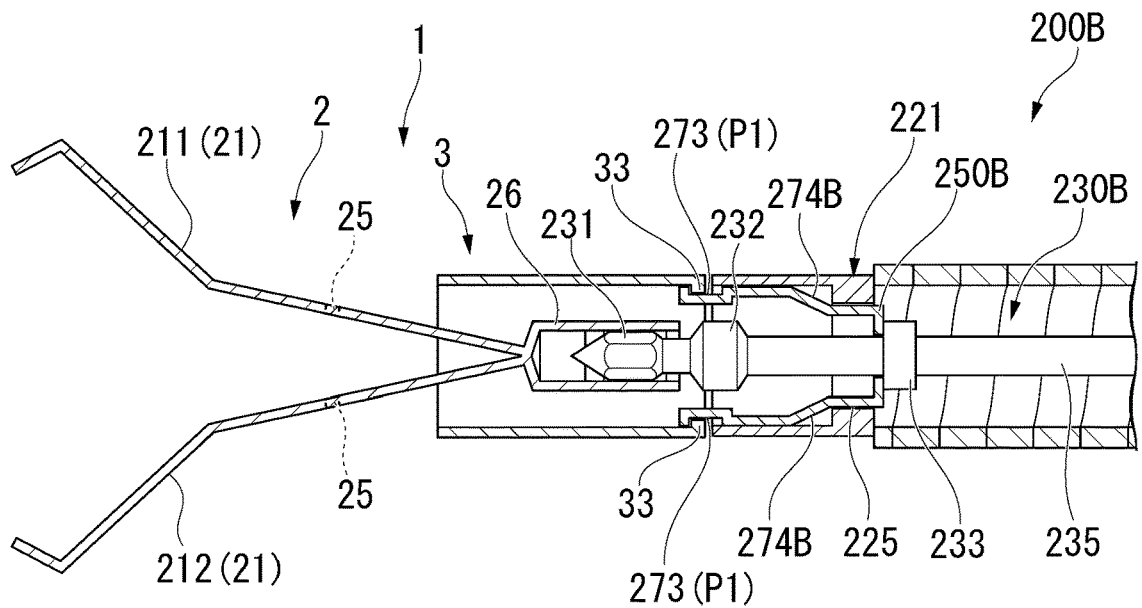
FIG. 16 is a cross-sectional view showing the clip introduction device that is connected to a pressing tube of the clip unit.

FIG. 16 is a cross-sectional view showing the clip introduction device 200B that is connected to the pressing tube 3. The user pushes the clip unit 1 toward the clip introduction device 200B from the distal-end side A1 so as to engage the hooking portion 273 protruding from the distal-end tube portion 221 toward the distal-end side A1 with the decreased-diameter portion 33 of the pressing tube 3. At this time, the second enlarged-diameter portion 233 is supporting the connection member 250B from the proximal-end side A2 and the connection member 250B does not move to the proximal-end side A2. The connection member 250B has the elasticity so as to tend to return to the initial position. At this time, the hooking portion 273 moves outwardly in the radial direction to be disposed at a position (the first position P1) where the hooking portion 273 engages with the decreased-diameter portion 33 from the inside of the radial direction.

The user advances the operation wire 230B to connect the proximal-end portion 26 of the clip 2 and the arrowhead hook 231. As a result, the clip unit 1 is loaded inside the clip introduction device 200.

Figure 17:
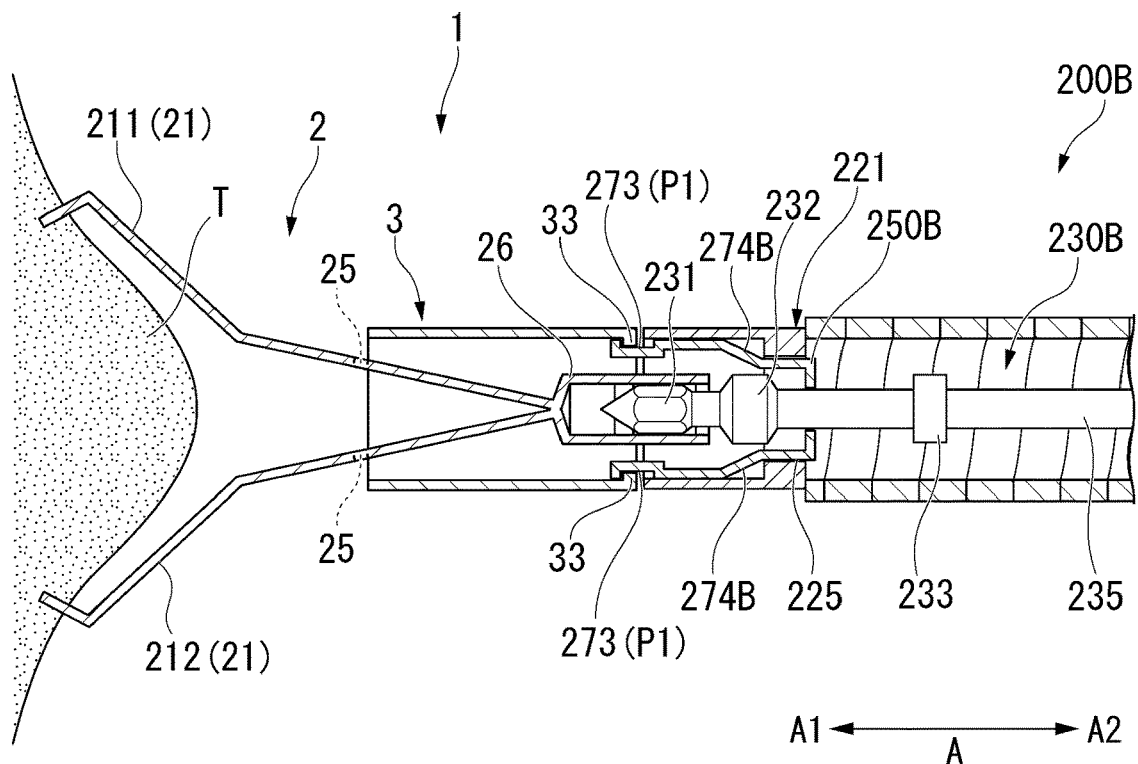
FIG. 17 is a cross-sectional view showing the clip introduction device in which the clip unit is loaded.

FIG. 17 is a cross-sectional view showing the clip introduction device 200B into which the clip unit 1 is loaded. The user introduces the clip unit 1 that is loaded in the clip introduction device 200B into the body through the channel of the endoscope. The user operates the operation portion 240 to grasp the tissue T by the clip 2.

The user retracts the slider 242 along the operation portion main body 241 such that the arrowhead hook 231 is retracted. By pulling the proximal-end portion 26 of the clip 2 to the proximal-end side A2, the pair of arms 21 are retracted into the pressing tube 3 and the pair of arms 21 are gradually closed. In this state, when the pulling force to the proximal-end portion 26 is released, due to the self-expanding force of the pair of arms 21, the clip 2 moves to the distal-end side A1 while returning to the open state. It is possible for the user to make the pair of arms 21 to return to the open state to re-grasp the tissue T.

Figure 18:
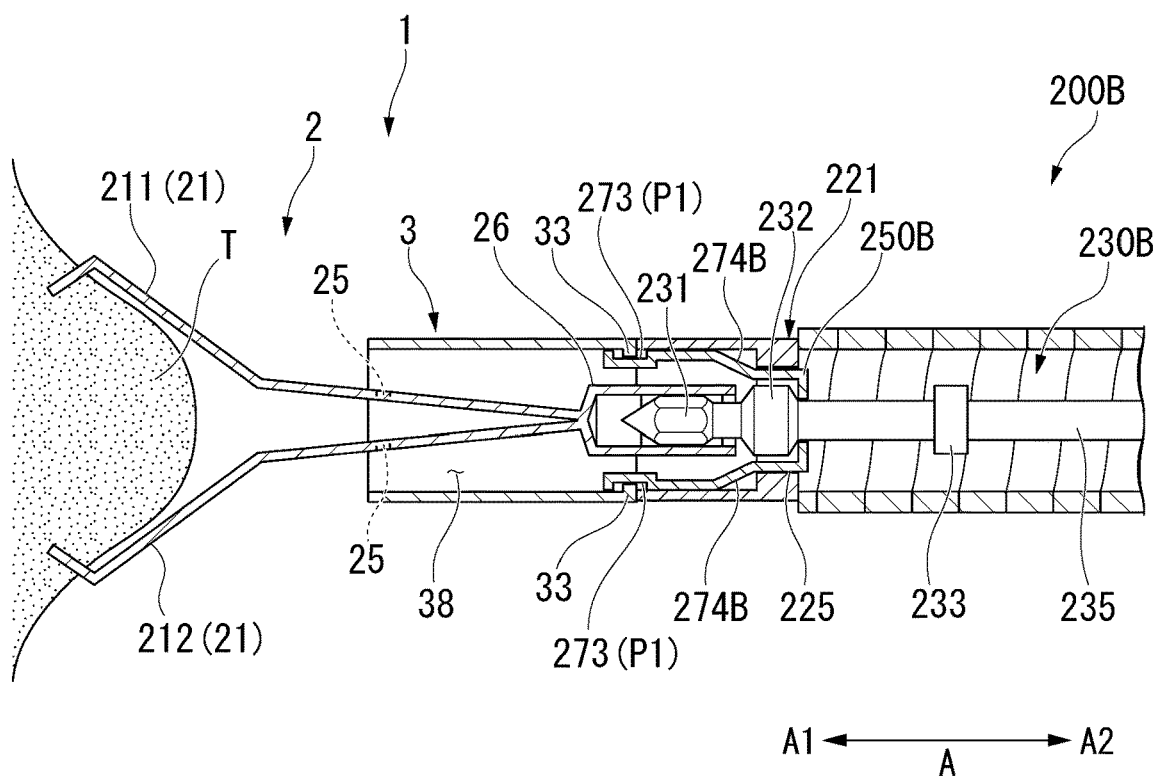
FIG. 18 is a cross-sectional view showing the clip unit where the clip is locked and the clip introduction device.

FIG. 18 is a cross-sectional view showing the clip unit 1 where the clip 2 is locked and the clip introduction device 200B. By further pulling the proximal-end portion 26 toward the proximal-end side A2, the engaging portion 25 is retracted into the internal space 38 of the pressing tube 3. When the engaging portion 25 is retracted into the internal space 38 of the pressing tube 3, the engaging portion 25 and the inner circumferential surface 32 of the pressing tube 3 are engaged with each other. As a result, the movement of the clip 2 toward the distal-end side A1 with respect to the pressing tube 3 is restricted and the pair of arms 21 are locked in the closed state. When the pair of arms 21 are locked in the closed state, it is impossible for the pair of arms 21 to return to the open state.

Figure 19:
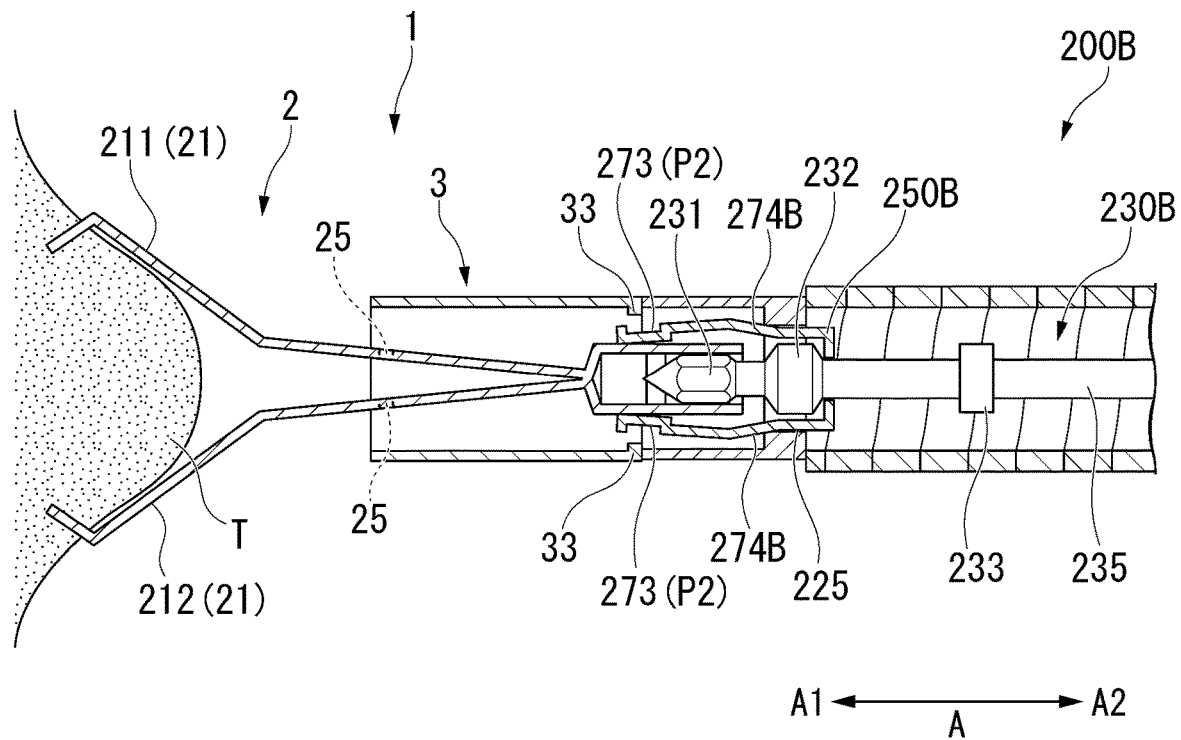
FIG. 19 is a cross-sectional view showing the clip introduction device where the arrowhead hook is further pulled.

FIG. 19 is a cross-sectional view showing the clip introduction device 200B where the arrowhead hook 231 is further pulled. The engaging portion 25 and the inner circumferential surface 32 of the pressing tube 3 are engaged with each other and the pair of arms 21 are locked in the closed state such that the clip 2 is not further pulled toward the proximal-end side A2. The arrowhead hook 231 of the pulled operation wire 230B is separated from the proximal-end portion 26 to be pulled toward the proximal-end side A2.

The enlarged-diameter portion 232 of the pulled operation wire 230B passes through the proximal-end opening portion 225 of the distal-end tube portion 221 to move toward the proximal-end side A2. The enlarged-diameter portion 232 of the operation wire 230B passing through the proximal-end opening portion 225 moves the connection member 250B toward the proximal-end side A2.

The distance between the distal ends of the deformation portions 274B is larger than the outer diameter D5 of the proximal-end opening portion 225 (D3>D5). Accordingly, the proximal-end opening portion 225 comes into contact with the deformation portions 274B to make the deformation portions 274B to deform inwardly in the radial direction so as to approach the central axis O2. As a result, the hooking portion 273 at the distal-end side moves to a position (the second position P2) at the inside in the radial direction with respect to the first position P1. In other words, the distal-end portion of the connection member 250 is decreased in the dimeter. The hooking portion 273 that is disposed at the second position P2 is in the state in which the hooking portion 273 is not engaged with the decreased-diameter portion 33, or the state in which the engagement with the decreased-diameter portion 33 is easy to be released.

Figure 20:
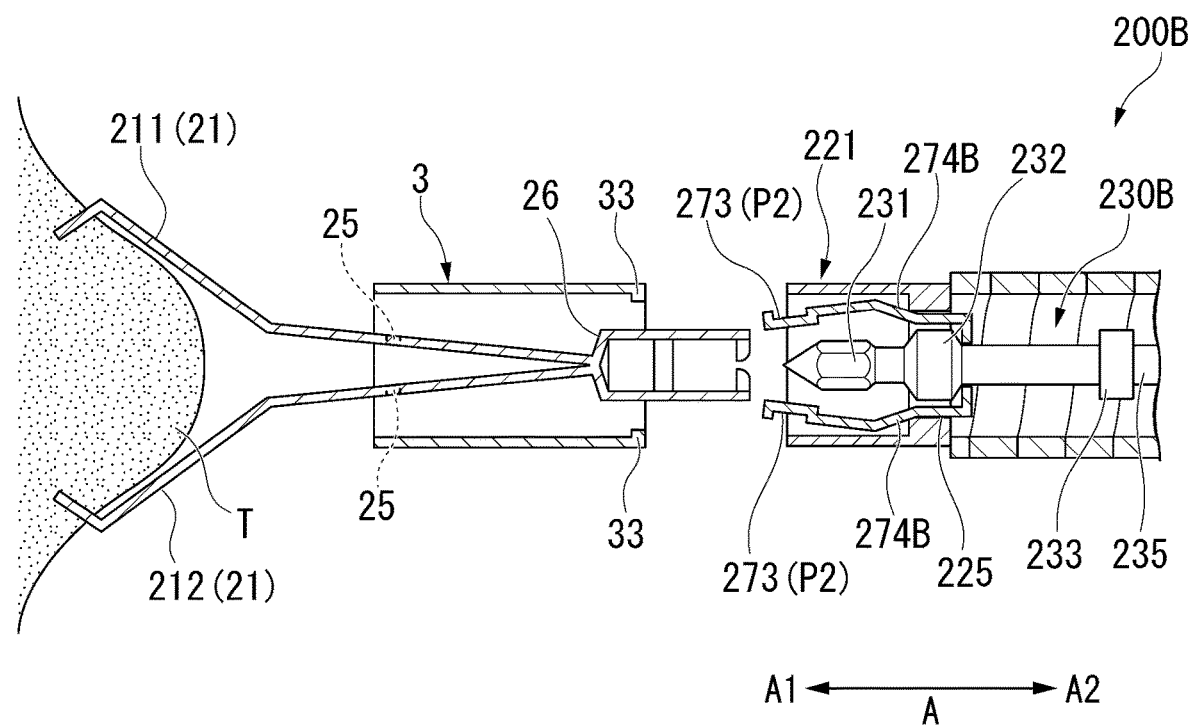
FIG. 20 is a cross-sectional view showing the clip introduction device from which the clip unit is separated.

FIG. 20 is a cross-sectional view showing the clip introduction device 200B from which the clip unit 1 is separated. The user further pulls the clip 2. The engagement between the decreased-diameter portion 33 and the hooking portion 273 is disengaged such that the clip unit 1 and the clip introduction device 200B are separated. The user retracts the sheath 220 to indwell the clip unit 1 in the state of ligating the tissue inside the body.

The user advances the arrowhead hook 231 to advance the connection member 250B by the second enlarged-diameter portion 233 so as to return the connection arm 270B to the initial position where the connection arm 270B is engageable with the pressing tube 3.

According to the clip delivery device and the clip introduction device 200B according to the present embodiment, it is possible for the clip 2 of the clip unit 1 to re-grasp the tissue (re-opening) such that the loading and the separation of the clip unit 1 with respect to the clip introduction device 200B can be definitely performed.

As described above, the second embodiment of the present disclosure has been described in detail with reference to the drawings; however, the specific configuration is not limited to the present embodiment, and design changes and the like are included within the scope of the present disclosure. Also, the configurational elements shown in the present embodiment and the modification examples shown below can be combined as appropriate.

Third Embodiment

A third embodiment of the present disclosure will be described by referring from FIG. 21 to FIG. 27. In the following description, the described configurations and the common configurations will be designated with the same reference signs and the duplicate description will be omitted. The clip delivery device according to the third embodiment is different from the clip delivery device 300 according to the first embodiment in the connection member 250.

The clip delivery device according to the third embodiment includes a clip introduction device (applicator) 200C and the clip unit 1. The clip introduction device (applicator) 200C includes the sheath 220, the operation wire 230, the operation portion 240, and a connection member 250C.

Figure 21:
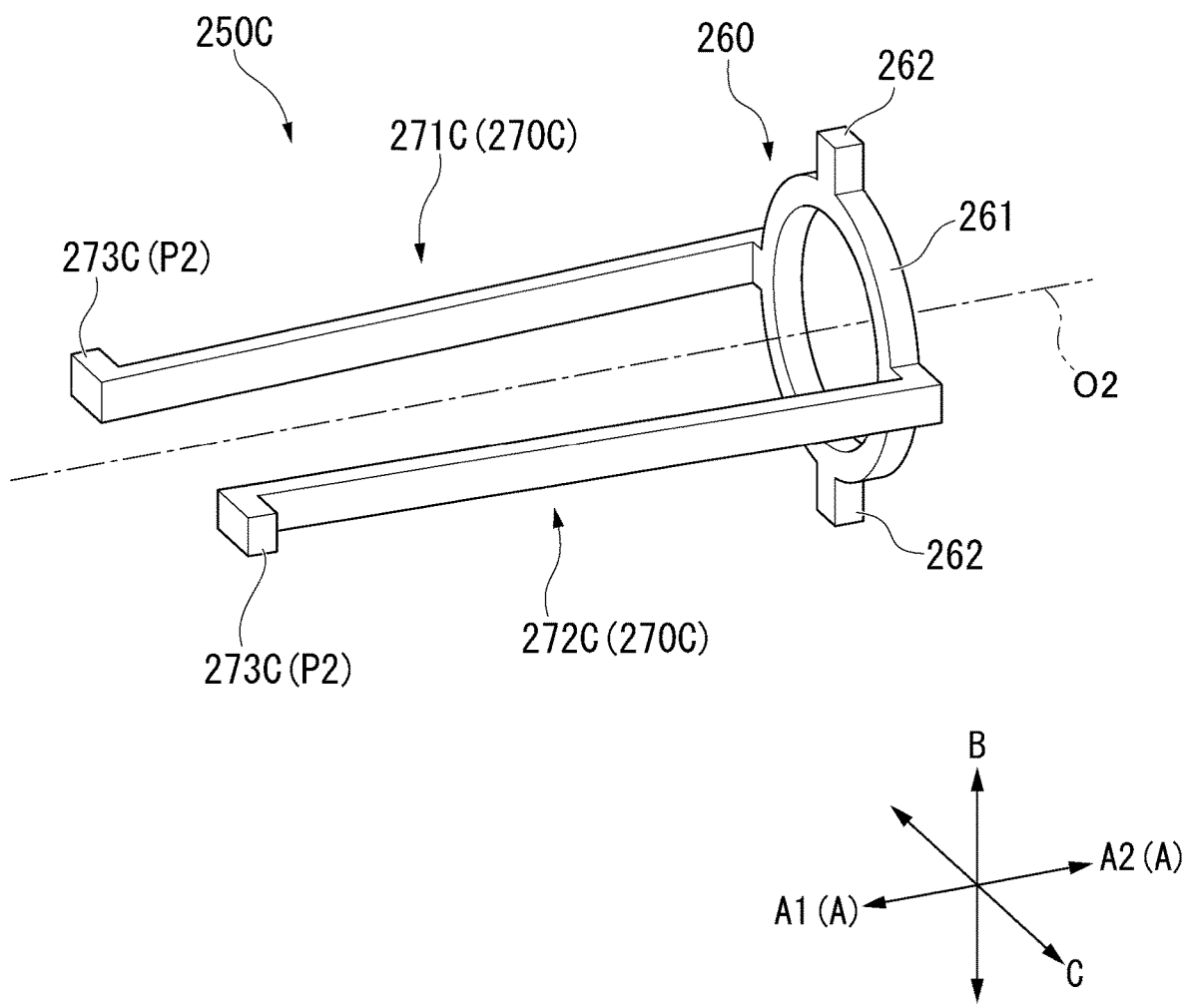
FIG. 21 is a perspective view showing a connection member in a clip introduction device of a clip delivery device according to a third embodiment.

FIG. 21 is a perspective view showing the connection portion 250C.

The connection portion 250C includes the support portion 260 and a connection arm 270C. The proximal end of the connection arm 270C (first connection arm 271C and second connection arm 272C) is attached to the support portion 260.

The connection arm 270C is arranged at both sides in the left-right direction C orthogonal to the longitudinal direction A and the up-down direction B. The first connection arm 271C and the second connection arm 272C are formed in a shape symmetrical with respect to the central axis O2 in the longitudinal direction A of the connection member 250C.

The connection arm 270C (first connection arm 271C and second connection arm 272C) includes a hooking portion 273C.

The hooking portion (hook) 273C is a hook bending outwardly in the radial direction, and is provided at the distal end of the connection arm 270C. The hooking portion 273C protrudes from the distal-end tube portion 221 toward the distal-end side A1. The hooking portion 273C is engageable with the decreased-diameter portion 33 of the pressing tube 3.

The connection arm 270C (first connection arm 271C and second connection arm 272C) has the elasticity and is movable at least in the left-right direction C. In the present embodiment, in the state without receiving any external force, the connection arm 270C is arranged at a position (the initial position) where the first connection arm 271C and the second connection arm 272C approach each other as toward the distal-end side A1.

Next, the operations and effect of the clip delivery device according to the present embodiment will be described by referring from FIG. 22 to FIG. 27.

Figure 22:
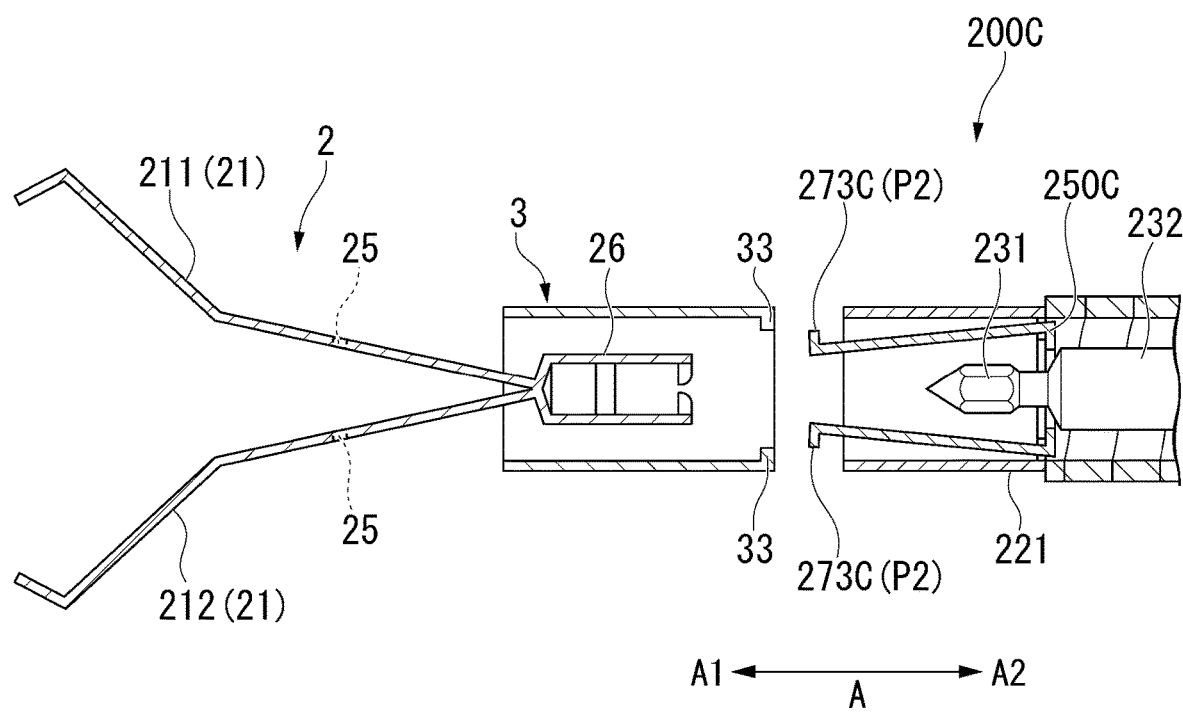
FIG. 22 is a cross-sectional view showing the clip introduction device before loading the clip unit.

FIG. 22 is a cross-sectional view showing the clip introduction device 200C before loading the clip unit 1. Before loading the clip unit 1, the connection arm 270C of the connection member 250C is disposed at the initial position.

Figure 23:
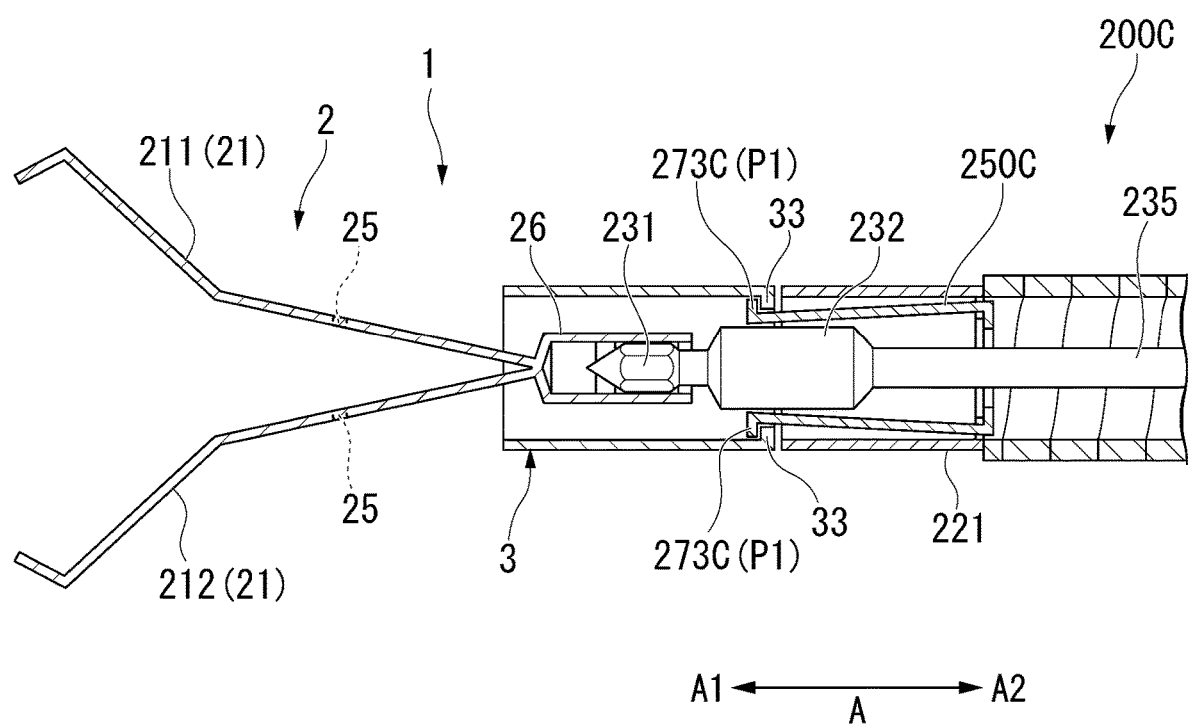
FIG. 23 is a cross-sectional view showing the clip introduction device that is connected to a pressing tube of the clip unit.

FIG. 23 is a cross-sectional view showing the clip introduction device 200C that is connected to the pressing tube 3. The user advances the operation wire 230 in the state of pushing the clip unit 1 toward the clip introduction device 200C from the distal-end side A1. The hooking portion 273 protruding from the distal-end tube portion 221 toward the distal-end side A1 is pushed to the outside in the radial direction and disposed at a position (the first position P1) to be engaged with the decreased-diameter portion 33 from the inside in the radial direction since the advanced enlarged-diameter portion 232 comes into contact with the connection arm 270C.

The user advances the operation wire 230 to connect the proximal-end portion 26 of the clip 2 and the arrowhead hook 231. As a result, the clip unit 1 is loaded inside the clip introduction device 200C.

Figure 24:
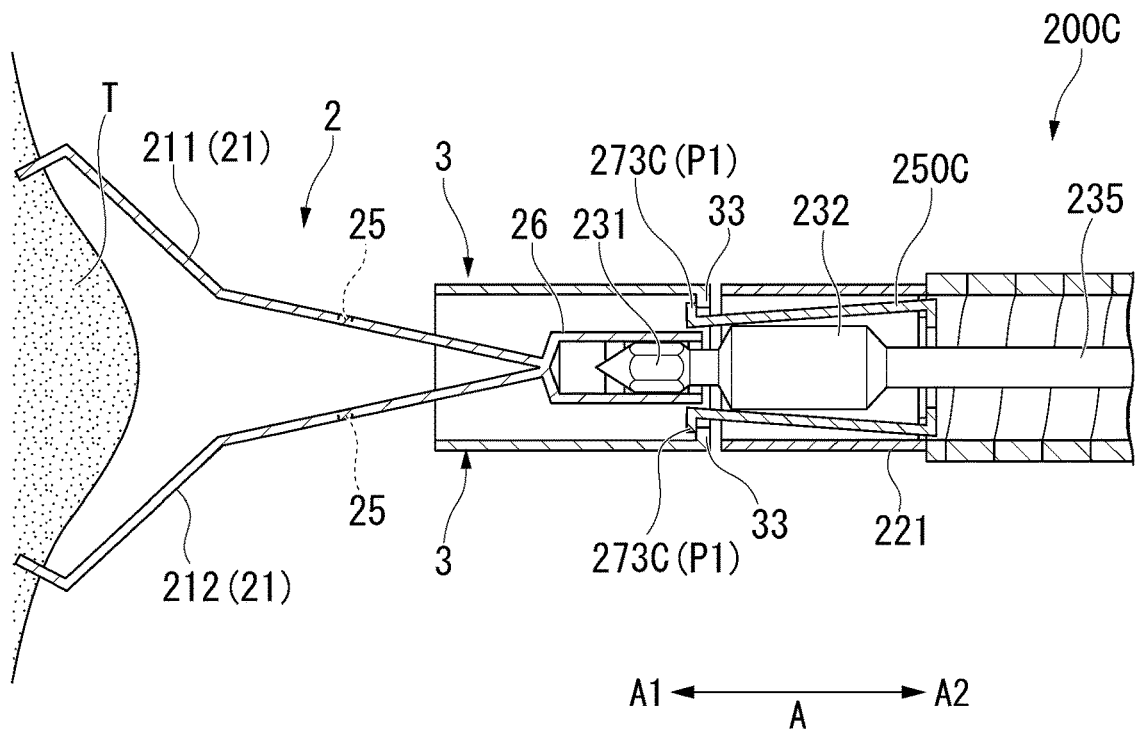
FIG. 24 is a cross-sectional view showing the clip introduction device in which the clip unit is loaded.

FIG. 24 is a cross-sectional view showing the clip introduction device 200C into which the clip unit 1 is loaded. The user introduces the clip unit 1 that is loaded in the clip introduction device 200C into the body through the channel of the endoscope. The user operates the operation portion 240 to grasp the tissue T by the clip 2.

The user retracts the slider 242 along the operation portion main body 241 such that the arrowhead hook 231 is retracted. By pulling the proximal-end portion 26 of the clip 2 to the proximal-end side A2, the pair of arms 21 are retracted into the pressing tube 3 and the pair of arms 21 are gradually closed. In this state, when the pulling force to the proximal-end portion 26 is released, due to the self-expanding force of the pair of arms 21, the clip 2 moves to the distal-end side A1 while returning to the open state. It is possible for the user to make the pair of arms 21 to return to the open state to re-grasp the tissue T.

Figure 25:
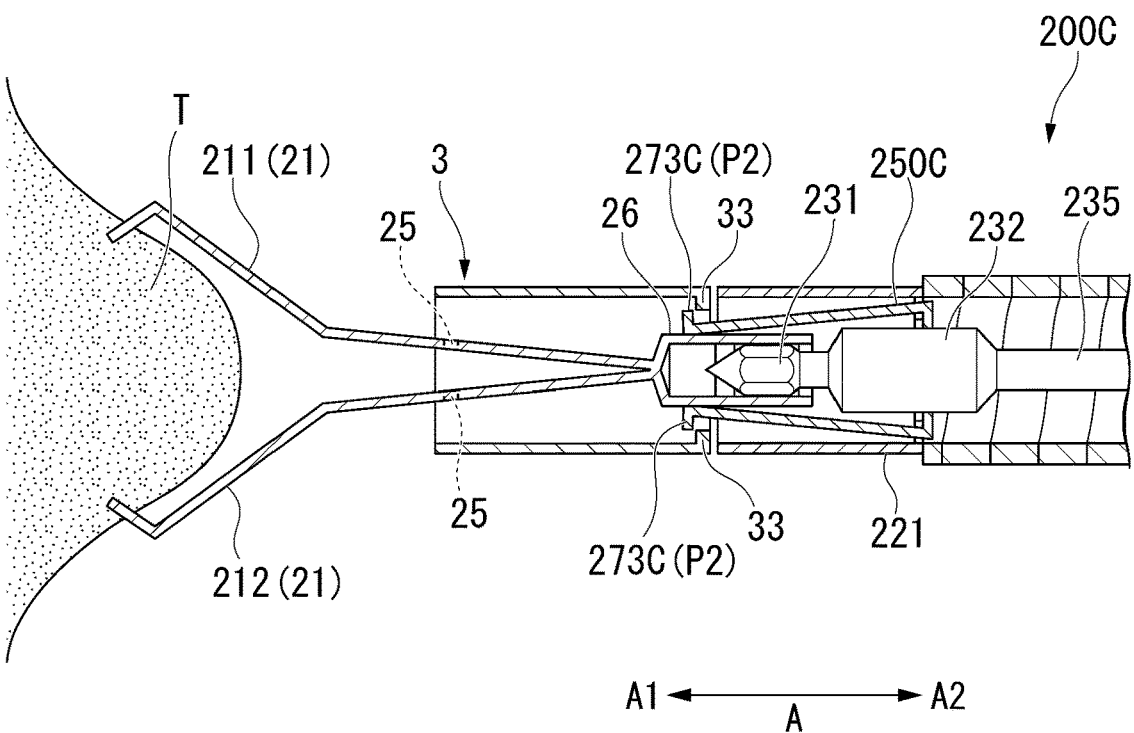
FIG. 25 is a cross-sectional view showing the clip unit where the clip is locked and the clip introduction device.

FIG. 25 is a cross-sectional view showing the clip unit 1 where the clip 2 is locked and the clip introduction device 200C. By further pulling the proximal-end portion 26 toward the proximal-end side A2, the engaging portion 25 is retracted into the internal space 38 of the pressing tube 3. When the engaging portion 25 is retracted into the internal space 38 of the pressing tube 3, the engaging portion 25 and the inner circumferential surface 32 of the pressing tube 3 are engaged with each other. As a result, the movement of the clip 2 toward the distal-end side A1 with respect to the pressing tube 3 is restricted and the pair of arms 21 are locked in the closed state. When the pair of arms 21 are locked in the closed state, it is impossible for the pair of arms 21 to return to the open state.

The retracted enlarged-diameter portion 232 separates from the connection arm 270C to not to be in contact with the connection arm 270C. The connection member 250C has the elasticity to tend to return to the initial position. As a result, the hooking portion 273C at the distal-end side moves to the position (the second position P2) at the inside of the radial direction with respect to the first position P1. In other words, the distal-end portion of the connection member 250C is decreased in the diameter. The hooking portion 273 that is disposed at the second position P2 is in the state in which the hooking portion 273 is not engaged with the decreased-diameter portion 33, or the state in which the engagement with the decreased-diameter portion 33 is easy to be released.

Figure 26:
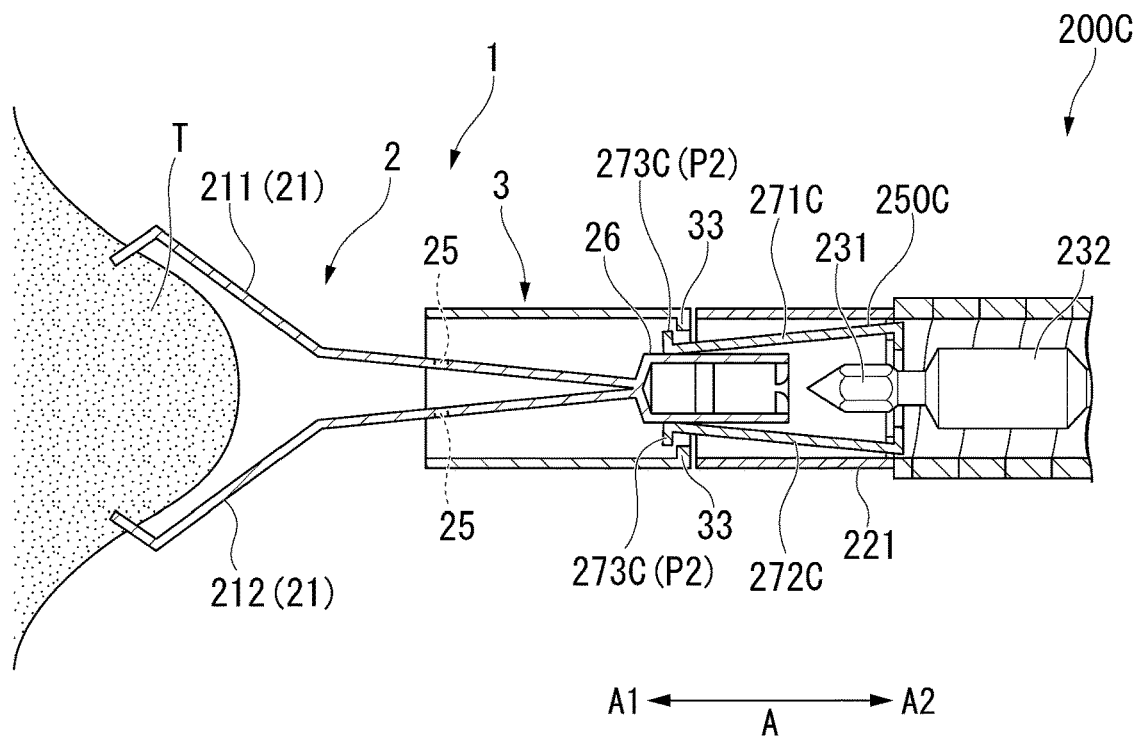
FIG. 26 is a cross-sectional view showing the clip introduction device where the arrowhead hook is further pulled.

FIG. 26 is a cross-sectional view showing the clip introduction device 200C from which the arrowhead hook 231 is further pulled. The engaging portion 25 and the inner circumferential surface 32 of the pressing tube 3 are engaged with each other and the pair of arms 21 are locked in the closed state such that the clip 2 is not further pulled toward the proximal-end side A2. The arrowhead hook 231 of the pulled operation wire 230 is separated from the proximal-end portion 26 and pulled toward the proximal-end side A2.

Figure 27:
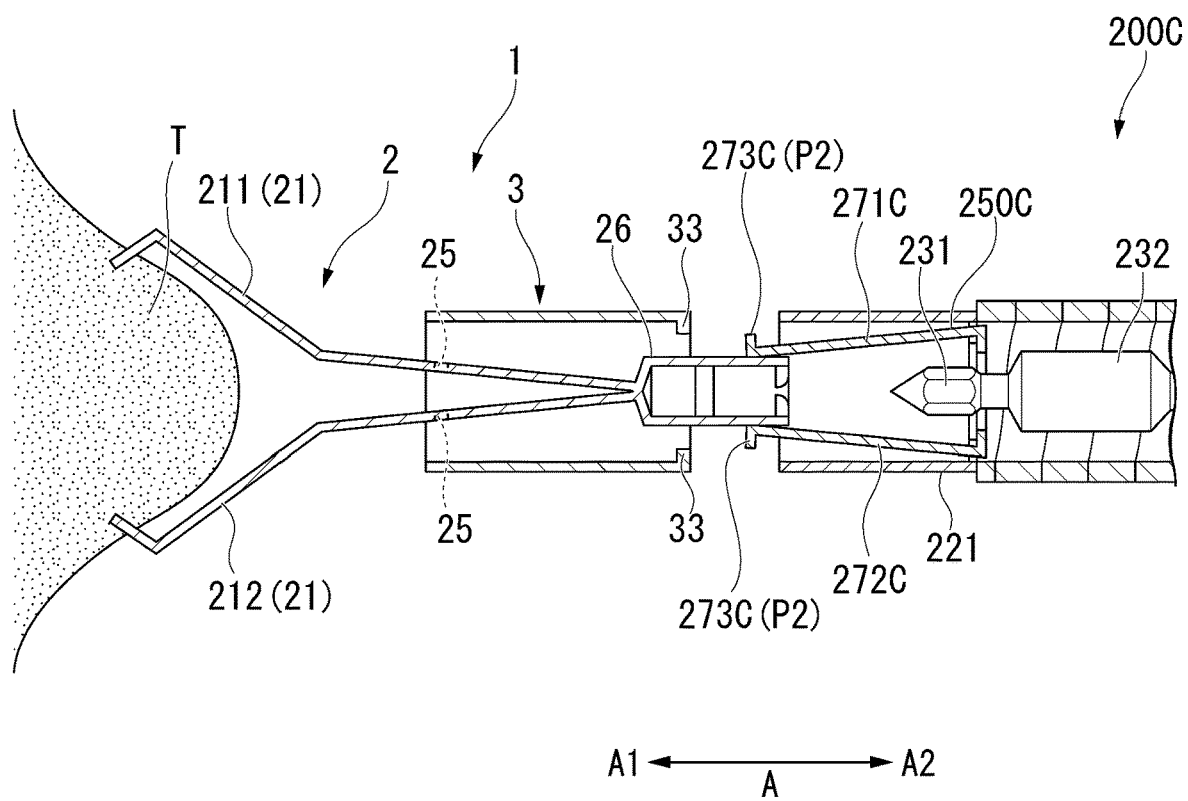
FIG. 27 is a cross-sectional view showing the clip introduction device from which the clip unit is separated.

FIG. 27 is a cross-sectional view showing the clip introduction device 200C from which the clip unit 1 is separated. The user further pulls the clip 2. The engagement between the decreased-diameter portion 33 and the hooking portion 273 is disengaged such that the clip unit 1 and the clip introduction device 200 are separated. The user retracts the sheath 220 to indwell the clip unit 1 in the state of ligating the tissue inside the body.

According to the clip delivery device and the clip introduction device 200C according to the present embodiment, it is possible for the clip 2 of the clip unit 1 to re-grasp the tissue (re-opening) such that the loading and the separation of the clip unit 1 with respect to the clip introduction device 200C can be definitely performed.

As described above, the third embodiment of the present disclosure has been described in detail with reference to the drawings; however, the specific configuration is not limited to the present embodiment, and design changes and the like are included within the scope of the present disclosure. Also, the configurational elements shown in the present embodiment and the modification examples shown above can be combined as appropriate.

What is claimed is:

1. A clip delivery device, comprising:
a sheath;
a wire inserted into the sheath;
a clip detachably connected to the wire and including a plurality of arms, wherein the plurality of arms is movable between an open position and a closed position;
a tube containing at least part of the clip and having a convex portion on an inner surface of the tube; and
a connector provided in the sheath and having a hook, the hook detachably connected with the convex portion of the tube,
wherein the tube is adjacent the sheath along a longitudinal axis,
wherein the hook is movable between a first position and a second position,
wherein, in the first position, the hook engages the convex portion of the tube and is located at a first radial distance from a central axis of the sheath,
wherein, in the second position, the hook is disengaged from the convex portion of the tube and is located at a second radial distance from the central axis of the sheath,
wherein the first radial distance is greater than the second radial distance, and
wherein, when the wire is moved proximal to the sheath, the hook is moved from the first position to the second position.

2. The clip delivery device according to claim 1, wherein the convex portion extends circumferentially around at least a portion of the inner surface of the tube, and
wherein the convex portion protrudes from the inner surface of the tube in a direction intersecting with the longitudinal axis.

3. The clip delivery device according to claim 1, wherein, when the hook is in the first position, the engagement of the hook with the convex portion connects the hook to the tube.

4. The clip delivery device according to claim 1, wherein at least part of the connector has an elasticity, and
wherein the hook is in the first position when no external force is applied to the hook.

5. The clip delivery device according to claim 4, wherein the connector includes a connection arm, and
wherein the connection arm includes:
the hook at a distal end of the connection arm, and
an elastically deformable deformation portion.

6. The clip delivery device according to claim 5, wherein the hook moving from the first position to the second position results from the wire elastically deforming the deformation portion when the wire is moved proximal to the sheath.

7. The clip delivery device according to claim 5, wherein the deformation portion is semicircular.

8. The clip delivery device according to claim 6, wherein the connector includes a support base having an annular shape,
wherein the wire passes through an opening in the annular shape,
wherein the connection arm is one of a plurality of connection arms, and
wherein proximal-end portions of the plurality of connection arms connect to the support base on different sides of the support base in a radial direction.

9. The clip delivery device according to claim 4, wherein the connector includes a connection arm,
wherein the connection arm includes:
the hook at a distal end of the connection arm, and
an elastically deformable deformation portion,
wherein the connection arm includes:
the hook at a distal end of the connection arm, and
an elastically deformable deformation portion, and
wherein, the hook moving from the first position to the second position results from the sheath elastically deforming the deformation portion when the wire is moved proximal to the sheath.

10. The clip delivery device according to claim 9, wherein the deformation portion has a tapered shape.

11. The clip delivery device according to claim 9, wherein the connector includes a support base having an annular shape,
wherein the wire passes through an opening in the annular shape, wherein the connection arm is one of a plurality of connection arms, and wherein proximal-end portions of the plurality of connection arms connect to the support base on different sides of the support base in a radial direction.

12. The clip delivery device according to claim 1, wherein at least part of the connector has an elasticity, and wherein the hook is in the second position when no external force is applied to the hook.

13. The clip delivery device according to claim 12, wherein the connector includes a connection arm, wherein the hook is at a distal end of the connection arm, and wherein, the hook moving from the second position to the first position results from the wire elastically deforming the deformation portion when the wire is moved distal to the sheath.

14. A clip delivery device, comprising:

a sheath;

a wire inserted into the sheath;

a clip detachably connected to the wire and including a plurality of arms, wherein the plurality of arms is movable between an open position and a closed position;

a tube containing at least part of the clip and having a convex portion on an inner surface of the tube; and a connector provided in the sheath and having a distal-end portion and a deformation portion, wherein the distal-end portion is detachably connected to the convex portion on an inner surface of the tube, wherein the deformation portion is elastically deformable, and wherein, when the wire is moved proximal to the sheath, the deformation portion is elastically deformed to decrease a diameter of the distal-end portion of the connector.

15. The clip delivery device according to claim 14, wherein the convex portion extends circumferentially around at least a portion of the inner surface of the tube, and wherein the convex portion protrudes from the inner surface of the tube in a direction intersecting with a longitudinal direction of the tube.

16. The clip delivery device according to claim 14, wherein the connector includes a connection arm, wherein the connection arm includes:

a hook at the distal end of the connection arm, and the deformation portion, and wherein, elastically deforming the deformation portion to decrease the diameter of the distal-end portion of the connector results from the wire engaging with the deformation portion to deform the deformation member to extend along a longitudinal direction of the connector when the wire is moved proximal to the sheath.

17. The clip delivery device according to claim 14, wherein the connector includes a connection arm, wherein the connection arm includes:

the distal end portion at a distal end of the connection arm, and the deformation portion, and wherein, elastically deforming the deformation portion to decrease the diameter of the distal-end portion of the connector results from the deformation portion deforming inwardly in a radial direction of the connector as the connector moves proximal to the sheath when the wire moves proximal to the sheath.

18. A method of releasing the clip of the clip delivery device according to claim 1, the method comprising:

moving the wire proximal to the sheath;

decreasing the diameter of the distal-end portion of the connector; and separating the clip from the connector and indwelling the tube and the clip.

19. The clip releasing method according to claim 18, further comprising engaging the wire and the connector, and deforming at least the deformation portion of the connector.

20. The clip unit releasing method according to claim 18, further comprising moving the connector proximal to the applicator, and deforming at least the deformation portion of the connector.

* * * * *